United States Patent
Pulé et al.

(10) Patent No.: US 11,466,070 B2
(45) Date of Patent: *Oct. 11, 2022

(54) SIGNALLING SYSTEM

(71) Applicant: AUTOLUS LIMITED, London (GB)

(72) Inventors: Martin Pulé, London (GB); Shaun Cordoba, London (GB); Simon Thomas, London (GB); Shimobi Onuoha, London (GB); Maria Stavrou, London (GB)

(73) Assignee: AUTOLUS LIMITED, London (GB)

( * ) Notice: Subject to any disclaimer, the term of this patent is extended or adjusted under 35 U.S.C. 154(b) by 413 days.

This patent is subject to a terminal disclaimer.

(21) Appl. No.: 16/076,760

(22) PCT Filed: Feb. 10, 2017

(86) PCT No.: PCT/GB2017/050340
§ 371 (c)(1),
(2) Date: Aug. 9, 2018

(87) PCT Pub. No.: WO2017/137758
PCT Pub. Date: Aug. 17, 2017

(65) Prior Publication Data
US 2019/0330299 A1    Oct. 31, 2019

(30) Foreign Application Priority Data
Feb. 12, 2016 (GB) ..................................... 1602563

(51) Int. Cl.
*C07K 14/725* (2006.01)
*A61K 35/17* (2015.01)
*C07K 14/73* (2006.01)
*C07K 16/28* (2006.01)

(52) U.S. Cl.
CPC .......... *C07K 14/7051* (2013.01); *A61K 35/17* (2013.01); *C07K 14/70514* (2013.01); *C07K 16/2803* (2013.01); *C07K 2319/02* (2013.01); *C07K 2319/03* (2013.01); *C07K 2319/60* (2013.01)

(58) Field of Classification Search
CPC ............ C07K 14/7051; C07K 2319/33; C07K 2319/70; A61K 35/17
See application file for complete search history.

(56) References Cited

U.S. PATENT DOCUMENTS 10,654,927 B2 * 5/2020 Pulé .................. C07K 14/7051
2017/0260269 A1    9/2017 Pulé et al.

FOREIGN PATENT DOCUMENTS

| WO | WO-2014/127261 A1 | 8/2014 | |
| WO | WO-2014127261 A1 * | 8/2014 | ........... C07K 14/705 |
| WO | WO-2015/150771 A1 | 10/2015 | |
| WO | WO-2016/030691 A1 | 3/2016 | |

OTHER PUBLICATIONS

Alex W. White, Andrew D. Westwell and Ghali Brahemi (2008) Protein-protein interactions as targets for small-molecule therapeutics in cancer. Expert Rev. Mol. Med. vol. 10, e8, Mar. 2008, (Year: 2008).*
U.S. Appl. No. 15/506,383, (US 2017-0260269 A1), filed Feb. 24, 2017.
Fanning et al., An anti-hapten camelid antibody reveals a cryptic binding site with significant energetic contributions from a nonhypervariable loop, Protein Sci., 20(7):1196-207 (2011).
International Application No. PCT/GB2017/050340, International Preliminary Report on Patentability, dated Aug. 14, 2018.
International Application No. PCT/GB2017/050340, International Search Report and Written Opinion, dated May 15, 2017.
Klotzsche et al., A peptide triggers allostery in tet repressor by binding to a unique site, J. Biol. Chem., 280(26):24591-9 (2005).
Luckner et al., How an agonist peptide mimics the antibiotic tetracycline to induce Tet-repressor, J. Mol. Biol., 368(3):780-90 (2007).
Miura et al., Peptides binding to a Gb3 mimic selected from a phage library, Biochim. Biophys. Acta, 1673(3):131-8 (2004).
Reverdatto et al., Peptide aptamers: development and applications, Curr. Top. Med. Chem., 15(12):1082-101 (2015).
Sun et al., The quest for spatio-temporal control of CAR T cells, Cell Res., 25(12):1281-2 (2015).
Ullman et al., In vitro methods for peptide display and their applications, Brief Funct. Genomics, 10(3):125-34 (2011).
Wu et al., Remote control of therapeutic T cells through a small molecule-gated chimeric receptor, Science, 350(6258):aab4077 (2015).

* cited by examiner

Primary Examiner — Amy E Juedes
Assistant Examiner — Brian Hartnett
(74) Attorney, Agent, or Firm — Marshall, Gerstein & Borun LLP

(57) ABSTRACT

The present invention provides a chimeric antigen receptor (CAR) system comprising; (i) a receptor component comprising a antigen binding domain and a first binding domain; and (ii) a signalling component comprising a signalling domain and a second binding domain which binds the single domain binder of the first binding domain of the receptor component wherein either the first or second binding domains comprise a single domain binder, and wherein, binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain.

12 Claims, 17 Drawing Sheets
Specification includes a Sequence Listing.

(a) WTWNAYAFAAPS-GGGS-[Protein]

(b)

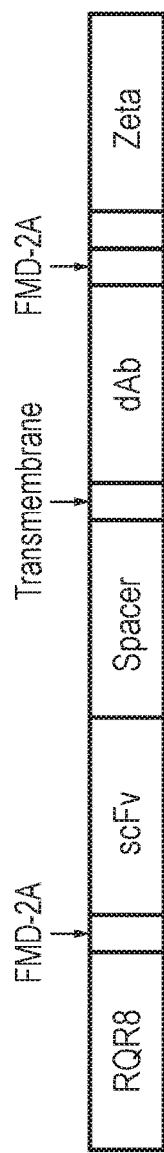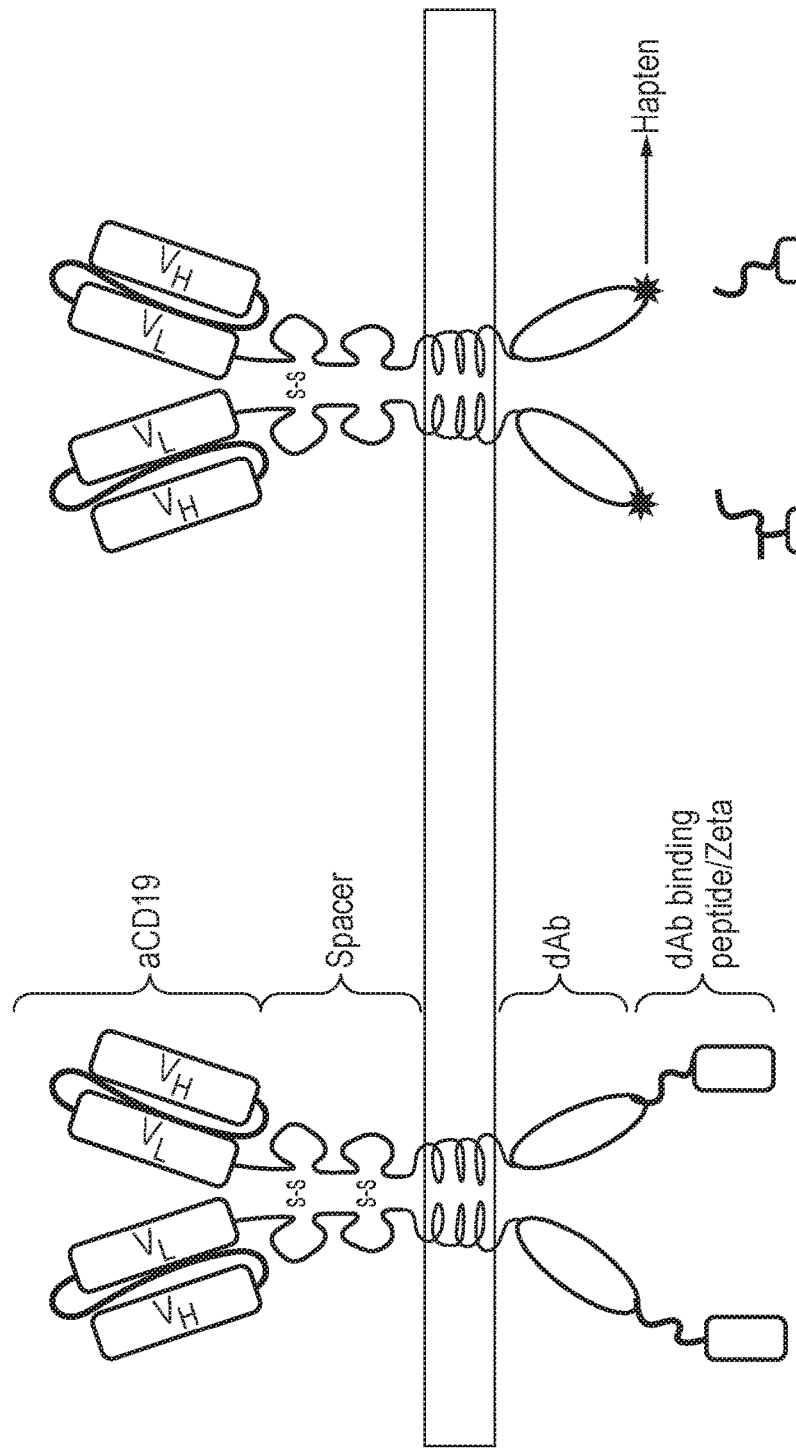
FIG. 16A
FIG. 16B

SEQUENCE LISTING

<160> NUMBER OF SEQ ID NOS: 37

<210> SEQ ID NO 1
<211> LENGTH: 112
<212> TYPE: PRT
<213> ORGANISM: Artificial Sequence
<220> FEATURE:
<223> OTHER INFORMATION: CD3 Z endodomain

<400> SEQUENCE: 1

```
Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 2
<211> LENGTH: 152
<212> TYPE: PRT
<213> ORGANISM: Artificial Sequence
<220> FEATURE:
<223> OTHER INFORMATION: CD28 and CD3 Zeta endodomains

<400> SEQUENCE: 2

```
Ser Lys Arg Ser Arg Leu Leu His Ser Asp Tyr Met Asn Met Thr Pro
1               5                  10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
        35                  40                  45

Asp Ala Pro Ala Tyr Gln Gln Gly Gln Asn Gln Leu Tyr Asn Glu Leu
    50                  55                  60

Asn Leu Gly Arg Arg Glu Glu Tyr Asp Val Leu Asp Lys Arg Arg Gly
65                  70                  75                  80

Arg Asp Pro Glu Met Gly Gly Lys Pro Arg Arg Lys Asn Pro Gln Glu
                85                  90                  95

Gly Leu Tyr Asn Glu Leu Gln Lys Asp Lys Met Ala Glu Ala Tyr Ser
            100                 105                 110

Glu Ile Gly Met Lys Gly Glu Arg Arg Arg Gly Lys Gly His Asp Gly
        115                 120                 125

Leu Tyr Gln Gly Leu Ser Thr Ala Thr Lys Asp Thr Tyr Asp Ala Leu
    130                 135                 140

His Met Gln Ala Leu Pro Pro Arg
145                 150
```

<210> SEQ ID NO 3
<211> LENGTH: 188
<212> TYPE: PRT
<213> ORGANISM: Artificial Sequence
<220> FEATURE:

<223> OTHER INFORMATION: CD28, OX40 and CD3 Zeta endodomains

<400> SEQUENCE: 3

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
        35                  40                  45

Ala His Lys Pro Pro Gly Gly Ser Phe Arg Thr Pro Ile Gln Glu
    50                  55                  60

Glu Gln Ala Asp Ala His Ser Thr Leu Ala Lys Ile Arg Val Lys Phe
65                  70                  75                  80

Ser Arg Ser Ala Asp Ala Pro Ala Tyr Gln Gln Gly Gln Asn Gln Leu
                85                  90                  95

Tyr Asn Glu Leu Asn Leu Gly Arg Arg Glu Glu Tyr Asp Val Leu Asp
            100                 105                 110

Lys Arg Arg Gly Arg Asp Pro Glu Met Gly Gly Lys Pro Arg Arg Lys
        115                 120                 125

Asn Pro Gln Glu Gly Leu Tyr Asn Glu Leu Gln Lys Asp Lys Met Ala
    130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
            180                 185
```

<210> SEQ ID NO 4
<211> LENGTH: 20
<212> TYPE: PRT
<213> ORGANISM: Foot-and-mouth disease virus

<400> SEQUENCE: 4

```
Arg Ala Glu Gly Arg Gly Ser Leu Leu Thr Cys Gly Asp Val Glu Glu
1               5                   10                  15

Asn Pro Gly Pro
            20
```

<210> SEQ ID NO 5
<211> LENGTH: 20
<212> TYPE: PRT
<213> ORGANISM: Foot-and-mouth disease virus

<400> SEQUENCE: 5

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 6
<211> LENGTH: 10
<212> TYPE: PRT
<213> ORGANISM: Artificial Sequence
<220> FEATURE:
<223> OTHER INFORMATION: single domain binder-interacting peptide
      (sdbiP) which binds a methotrexate dAb

<400> SEQUENCE: 6

```
Ala Cys Asn Ala Gly His Leu Ser Gln Cys
1               5                   10

<210> SEQ ID NO 7
<211> LENGTH: 7
<212> TYPE: PRT
<213> ORGANISM: Artificial Sequence
<220> FEATURE:
<223> OTHER INFORMATION: sdbiP which binds a methotrexate dAb

<400> SEQUENCE: 7

Ala Ser Leu Ala Ile Thr His
1               5

<210> SEQ ID NO 8
<211> LENGTH: 10
<212> TYPE: PRT
<213> ORGANISM: Artificial Sequence
<220> FEATURE:
<223> OTHER INFORMATION: sdbiP which binds a methotrexate dAb

<400> SEQUENCE: 8

Ala Cys Ile Ser Leu Thr Leu Asn Arg Cys
1               5                   10

<210> SEQ ID NO 9
<211> LENGTH: 7
<212> TYPE: PRT
<213> ORGANISM: Artificial Sequence
<220> FEATURE:
<223> OTHER INFORMATION: sdbiP which binds a methotrexate dAb

<400> SEQUENCE: 9

Gln Thr Glu Lys Asn Pro Leu
1               5

<210> SEQ ID NO 10
<211> LENGTH: 10
<212> TYPE: PRT
<213> ORGANISM: Artificial Sequence
<220> FEATURE:
<223> OTHER INFORMATION: sdbiP which binds a methotrexate dAb

<400> SEQUENCE: 10

Ala Cys Asn Ala Gly His Leu Ser Gln Cys
1               5                   10

<210> SEQ ID NO 11
<211> LENGTH: 119
<212> TYPE: PRT
<213> ORGANISM: Artificial Sequence
<220> FEATURE:
<223> OTHER INFORMATION: caffeine single domain binder

<400> SEQUENCE: 11

Glu Val Gln Leu Gln Ala Ser Gly Gly Gly Leu Val Gln Ala Gly Gly
1               5                   10                  15

Ser Leu Arg Leu Ser Cys Thr Ala Ser Gly Arg Thr Gly Thr Ile Tyr
            20                  25                  30

Ser Met Ala Trp Phe Arg Gln Ala Pro Gly Lys Glu Arg Glu Phe Leu
        35                  40                  45

Ala Thr Val Gly Trp Ser Ser Gly Ile Thr Tyr Tyr Met Asp Ser Val
    50                  55                  60

Lys Gly Arg Phe Thr Ile Ser Arg Asp Asn Ala Lys Asn Ser Ala Tyr
65                  70                  75                  80
```

```
Leu Gln Met Asn Ser Leu Lys Pro Glu Asp Thr Ala Val Tyr Tyr Cys
                85                  90                  95

Thr Ala Thr Arg Ala Tyr Ser Val Gly Tyr Asp Tyr Trp Gly Gln Gly
            100                 105                 110

Thr Gln Val Thr Val Ser Ser
        115

<210> SEQ ID NO 12
<211> LENGTH: 7
<212> TYPE: PRT
<213> ORGANISM: Artificial Sequence
<220> FEATURE:
<223> OTHER INFORMATION: sdbiP which binds a caffeine dAb

<400> SEQUENCE: 12

His Thr Leu Asn Lys Pro Pro
1               5

<210> SEQ ID NO 13
<211> LENGTH: 7
<212> TYPE: PRT
<213> ORGANISM: Artificial Sequence
<220> FEATURE:
<223> OTHER INFORMATION: sdbiP which binds a caffeine dAb

<400> SEQUENCE: 13

Asp Leu Ser Ile Gly Asn His
1               5

<210> SEQ ID NO 14
<211> LENGTH: 7
<212> TYPE: PRT
<213> ORGANISM: Artificial Sequence
<220> FEATURE:
<223> OTHER INFORMATION: sdbiP which binds a caffeine dAb

<400> SEQUENCE: 14

His Asp Ser Pro Thr Ala Ala
1               5

<210> SEQ ID NO 15
<211> LENGTH: 7
<212> TYPE: PRT
<213> ORGANISM: Artificial Sequence
<220> FEATURE:
<223> OTHER INFORMATION: sdbiP which binds a caffeine dAb

<400> SEQUENCE: 15

Tyr Pro Asp Val Pro Leu Ala
1               5

<210> SEQ ID NO 16
<211> LENGTH: 10
<212> TYPE: PRT
<213> ORGANISM: Artificial Sequence
<220> FEATURE:
<223> OTHER INFORMATION: sdbiP which binds a caffeine dAb

<400> SEQUENCE: 16

Ala Cys Thr Tyr Leu Asn Ser Ala Lys Cys
1               5                   10

<210> SEQ ID NO 17
<211> LENGTH: 8
<212> TYPE: PRT
```

<213> ORGANISM: Artificial Sequence
<220> FEATURE:
<223> OTHER INFORMATION: complementarity determining region (CDR), CDR1

<400> SEQUENCE: 17

Gly Arg Thr Phe Ser Ser Tyr Asn
1               5

<210> SEQ ID NO 18
<211> LENGTH: 8
<212> TYPE: PRT
<213> ORGANISM: Artificial Sequence
<220> FEATURE:
<223> OTHER INFORMATION: CDR2

<400> SEQUENCE: 18

Ile Ser Trp Ser Gly Ala Arg Thr
1               5

<210> SEQ ID NO 19
<211> LENGTH: 14
<212> TYPE: PRT
<213> ORGANISM: Artificial Sequence
<220> FEATURE:
<223> OTHER INFORMATION: CDR3

<400> SEQUENCE: 19

Ala Ala Gly Arg Gly Trp Gly Thr Glu Ala Ile Leu Asp Tyr
1               5                   10

<210> SEQ ID NO 20
<211> LENGTH: 8
<212> TYPE: PRT
<213> ORGANISM: Artificial Sequence
<220> FEATURE:
<223> OTHER INFORMATION: CDR1

<400> SEQUENCE: 20

Gly Arg Ser Leu Ser Ser Tyr Val
1               5

<210> SEQ ID NO 21
<211> LENGTH: 14
<212> TYPE: PRT
<213> ORGANISM: Artificial Sequence
<220> FEATURE:
<223> OTHER INFORMATION: CDR3

<400> SEQUENCE: 21

Val Ala Gly Arg Gly Trp Gly Thr Glu Ala Ile Leu Asp Tyr
1               5                   10

<210> SEQ ID NO 22
<211> LENGTH: 8
<212> TYPE: PRT
<213> ORGANISM: Artificial Sequence
<220> FEATURE:
<223> OTHER INFORMATION: CDR1

<400> SEQUENCE: 22

Gly Arg Thr Phe Ser Asn Tyr Asn
1               5

<210> SEQ ID NO 23
<211> LENGTH: 8
<212> TYPE: PRT
<213> ORGANISM: Artificial Sequence

```
<220> FEATURE:
<223> OTHER INFORMATION: CDR2

<400> SEQUENCE: 23

Ile Asn Trp Ser Gly Gly Arg Thr
1               5

<210> SEQ ID NO 24
<211> LENGTH: 8
<212> TYPE: PRT
<213> ORGANISM: Artificial Sequence
<220> FEATURE:
<223> OTHER INFORMATION: CDR1

<400> SEQUENCE: 24

Gly Arg Thr Phe Ser Arg Tyr Asn
1               5

<210> SEQ ID NO 25
<211> LENGTH: 8
<212> TYPE: PRT
<213> ORGANISM: Artificial Sequence
<220> FEATURE:
<223> OTHER INFORMATION: CDR2

<400> SEQUENCE: 25

Ile Ser Arg Ser Gly Gly Ile Thr
1               5

<210> SEQ ID NO 26
<211> LENGTH: 14
<212> TYPE: PRT
<213> ORGANISM: Artificial Sequence
<220> FEATURE:
<223> OTHER INFORMATION: CDR3

<400> SEQUENCE: 26

Ala Ala Gly Arg Gly Trp Gly Val Glu Ala Ile Leu Asp Tyr
1               5                   10

<210> SEQ ID NO 27
<211> LENGTH: 8
<212> TYPE: PRT
<213> ORGANISM: Artificial Sequence
<220> FEATURE:
<223> OTHER INFORMATION: CDR1

<400> SEQUENCE: 27

Gly Asn Ile Gly Leu Val Ser Val
1               5

<210> SEQ ID NO 28
<211> LENGTH: 7
<212> TYPE: PRT
<213> ORGANISM: Artificial Sequence
<220> FEATURE:
<223> OTHER INFORMATION: CDR2

<400> SEQUENCE: 28

Ile Thr Gly Gly Gly Ser Thr
1               5

<210> SEQ ID NO 29
<211> LENGTH: 9
<212> TYPE: PRT
<213> ORGANISM: Artificial Sequence
<220> FEATURE:
```

<223> OTHER INFORMATION: CDR3

<400> SEQUENCE: 29

Arg Leu Val Asn Asn Gly Arg Pro Phe
1               5

<210> SEQ ID NO 30
<211> LENGTH: 9
<212> TYPE: PRT
<213> ORGANISM: Artificial Sequence
<220> FEATURE:
<223> OTHER INFORMATION: CDR1

<400> SEQUENCE: 30

Gly Arg Leu Ser Leu Ser Ser Tyr Val
1               5

<210> SEQ ID NO 31
<211> LENGTH: 6
<212> TYPE: PRT
<213> ORGANISM: Artificial Sequence
<220> FEATURE:
<223> OTHER INFORMATION: Caffeine dAb CDR1

<400> SEQUENCE: 31

Thr Ile Tyr Ser Met Ala
1               5

<210> SEQ ID NO 32
<211> LENGTH: 17
<212> TYPE: PRT
<213> ORGANISM: Artificial Sequence
<220> FEATURE:
<223> OTHER INFORMATION: Caffeine dAb CDR2

<400> SEQUENCE: 32

Thr Val Gly Trp Ser Ser Gly Ile Thr Tyr Tyr Met Asp Ser Val Lys
1               5                   10                  15

Gly

<210> SEQ ID NO 33
<211> LENGTH: 10
<212> TYPE: PRT
<213> ORGANISM: Artificial Sequence
<220> FEATURE:
<223> OTHER INFORMATION: Caffeine dAb CDR3

<400> SEQUENCE: 33

Thr Arg Ala Tyr Ser Val Gly Tyr Asp Tyr
1               5                   10

<210> SEQ ID NO 34
<211> LENGTH: 16
<212> TYPE: PRT
<213> ORGANISM: Artificial Sequence
<220> FEATURE:
<223> OTHER INFORMATION: TetR interacting peptide (TiP)

<400> SEQUENCE: 34

Trp Thr Trp Asn Ala Tyr Ala Phe Ala Ala Pro Ser Gly Gly Gly Ser
1               5                   10                  15

<210> SEQ ID NO 35
<211> LENGTH: 87
<212> TYPE: PRT
<213> ORGANISM: Artificial Sequence

```
<220> FEATURE:
<223> OTHER INFORMATION: intracellular linker domain derived from CD4
      (WT)

<400> SEQUENCE: 35

Leu Ser Asp Ser Gly Gln Val Leu Leu Glu Ser Asn Ile Lys Val Leu
1               5                   10                  15

Pro Thr Trp Ser Thr Pro Val Gln Pro Met Ala Leu Ile Val Leu Gly
            20                  25                  30

Gly Val Ala Gly Leu Leu Leu Phe Ile Gly Leu Gly Ile Phe Phe Cys
        35                  40                  45

Val Arg Cys Arg His Arg Arg Gln Ala Glu Arg Met Ser Gln Ile
    50                  55                  60

Lys Arg Leu Leu Ser Glu Lys Lys Thr Cys Gln Cys Pro His Arg Phe
65              70                  75                  80

Gln Lys Thr Cys Ser Pro Ile
                85

<210> SEQ ID NO 36
<211> LENGTH: 61
<212> TYPE: PRT
<213> ORGANISM: Artificial Sequence
<220> FEATURE:
<223> OTHER INFORMATION: CD4 endodomain optimized for

<400> SEQUENCE: 36

Ala Leu Ile Val Leu Gly Gly Val Ala Gly Leu Leu Leu Phe Ile Gly
1               5                   10                  15

Leu Gly Ile Phe Phe Cys Val Arg Cys Arg His Arg Arg Gln Ala
            20                  25                  30

Glu Arg Met Ala Gln Ile Lys Arg Val Val Ser Glu Lys Lys Thr Ala
        35                  40                  45

Gln Ala Pro His Arg Phe Gln Lys Thr Cys Ser Pro Ile
    50                  55                  60

<210> SEQ ID NO 37
<211> LENGTH: 926
<212> TYPE: PRT
<213> ORGANISM: Artificial Sequence
<220> FEATURE:
<223> OTHER INFORMATION: TetCAR amino acid sequence

<400> SEQUENCE: 37

Met Trp Thr Trp Asn Ala Tyr Ala Phe Ala Ala Pro Ser Gly Gly Gly
1               5                   10                  15

Ser Ala Asp Ala Pro Ala Tyr Gln Gln Gly Gln Asn Gln Leu Tyr Asn
            20                  25                  30

Glu Leu Asn Leu Gly Arg Arg Glu Glu Tyr Asp Val Leu Asp Lys Arg
        35                  40                  45

Arg Gly Arg Asp Pro Glu Met Gly Gly Lys Pro Arg Arg Lys Asn Pro
    50                  55                  60

Gln Glu Gly Leu Tyr Asn Glu Leu Gln Lys Asp Lys Met Ala Glu Ala
65              70                  75                  80

Tyr Ser Glu Ile Gly Met Lys Gly Glu Arg Arg Arg Gly Lys Gly His
            85                  90                  95

Asp Gly Leu Tyr Gln Gly Leu Ser Thr Ala Thr Lys Asp Thr Tyr Asp
        100                 105                 110

Ala Leu His Met Gln Ala Leu Pro Pro Arg Arg Ala Glu Gly Arg Gly
    115                 120                 125
```

```
Ser Leu Leu Thr Cys Gly Asp Val Glu Glu Asn Pro Gly Pro Met Ala
    130                 135                 140

Val Pro Thr Gln Val Leu Gly Leu Leu Leu Trp Leu Thr Asp Ala
145                 150                 155                 160

Arg Cys Asp Ile Gln Met Thr Gln Ser Pro Ser Ser Leu Ser Ala Ser
                165                 170                 175

Val Gly Asp Arg Val Thr Ile Thr Cys Arg Ala Ser Glu Asp Ile Tyr
            180                 185                 190

Phe Asn Leu Val Trp Tyr Gln Gln Lys Pro Gly Lys Ala Pro Lys Leu
        195                 200                 205

Leu Ile Tyr Asp Thr Asn Arg Leu Ala Asp Gly Val Pro Ser Arg Phe
    210                 215                 220

Ser Gly Ser Gly Ser Gly Thr Gln Tyr Thr Leu Thr Ile Ser Ser Leu
225                 230                 235                 240

Gln Pro Glu Asp Phe Ala Thr Tyr Tyr Cys Gln His Tyr Lys Asn Tyr
                245                 250                 255

Pro Leu Thr Phe Gly Gln Gly Thr Lys Leu Glu Ile Lys Arg Ser Gly
            260                 265                 270

Gly Gly Gly Ser Gly Gly Gly Ser Gly Gly Gly Ser Gly Gly
        275                 280                 285

Gly Gly Ser Arg Ser Glu Val Gln Leu Val Glu Ser Gly Gly Gly Leu
    290                 295                 300

Val Gln Pro Gly Gly Ser Leu Arg Leu Ser Cys Ala Ala Ser Gly Phe
305                 310                 315                 320

Thr Leu Ser Asn Tyr Gly Met His Trp Ile Arg Gln Ala Pro Gly Lys
                325                 330                 335

Gly Leu Glu Trp Val Ser Ser Ile Ser Leu Asn Gly Gly Ser Thr Tyr
            340                 345                 350

Tyr Arg Asp Ser Val Lys Gly Arg Phe Thr Ile Ser Arg Asp Asn Ala
        355                 360                 365

Lys Ser Thr Leu Tyr Leu Gln Met Asn Ser Leu Arg Ala Glu Asp Thr
    370                 375                 380

Ala Val Tyr Tyr Cys Ala Ala Gln Asp Ala Tyr Thr Gly Gly Tyr Phe
385                 390                 395                 400

Asp Tyr Trp Gly Gln Gly Thr Leu Val Thr Val Ser Ser Met Asp Pro
                405                 410                 415

Ala Glu Pro Lys Ser Pro Asp Lys Thr His Thr Cys Pro Pro Cys Pro
            420                 425                 430

Ala Pro Pro Val Ala Gly Pro Ser Val Phe Leu Phe Pro Pro Lys Pro
        435                 440                 445

Lys Asp Thr Leu Met Ile Ala Arg Thr Pro Glu Val Thr Cys Val Val
    450                 455                 460

Val Asp Val Ser His Glu Asp Pro Glu Val Lys Phe Asn Trp Tyr Val
465                 470                 475                 480

Asp Gly Val Glu Val His Asn Ala Lys Thr Lys Pro Arg Glu Glu Gln
                485                 490                 495

Tyr Asn Ser Thr Tyr Arg Val Val Ser Val Leu Thr Val Leu His Gln
            500                 505                 510

Asp Trp Leu Asn Gly Lys Glu Tyr Lys Cys Lys Val Ser Asn Lys Ala
        515                 520                 525

Leu Pro Ala Pro Ile Glu Lys Thr Ile Ser Lys Ala Lys Gly Gln Pro
    530                 535                 540
```

-continued

```
Arg Glu Pro Gln Val Tyr Thr Leu Pro Pro Ser Arg Asp Glu Leu Thr
545                 550                 555                 560

Lys Asn Gln Val Ser Leu Thr Cys Leu Val Lys Gly Phe Tyr Pro Ser
                565                 570                 575

Asp Ile Ala Val Glu Trp Glu Ser Asn Gly Gln Pro Glu Asn Asn Tyr
                580                 585                 590

Lys Thr Thr Pro Pro Val Leu Asp Ser Asp Gly Ser Phe Phe Leu Tyr
                595                 600                 605

Ser Lys Leu Thr Val Asp Lys Ser Arg Trp Gln Gln Gly Asn Val Phe
                610                 615                 620

Ser Cys Ser Val Met His Glu Ala Leu His Asn His Tyr Thr Gln Lys
625                 630                 635                 640

Ser Leu Ser Leu Ser Pro Gly Lys Lys Asp Pro Met Ala Leu Ile Val
                645                 650                 655

Leu Gly Gly Val Ala Gly Leu Leu Leu Phe Ile Gly Leu Gly Ile Phe
                660                 665                 670

Phe Cys Val Arg Cys Arg His Arg Arg Arg Gln Ala Glu Arg Met Ala
                675                 680                 685

Gln Ile Lys Arg Val Val Ser Glu Lys Lys Thr Ala Gln Ala Pro His
690                 695                 700

Arg Phe Gln Lys Thr Cys Ser Pro Ile Ser Gly Gly Gly Ser Met
705                 710                 715                 720

Ser Arg Leu Asp Lys Ser Lys Val Ile Asn Ser Ala Leu Glu Leu Leu
                725                 730                 735

Asn Glu Val Gly Ile Glu Gly Leu Thr Thr Arg Lys Leu Ala Gln Lys
                740                 745                 750

Leu Gly Val Glu Gln Pro Thr Leu Tyr Trp His Val Lys Asn Lys Arg
                755                 760                 765

Ala Leu Leu Asp Ala Leu Ala Ile Glu Met Leu Asp Arg His His Thr
770                 775                 780

His Phe Cys Pro Leu Glu Gly Glu Ser Trp Gln Asp Phe Leu Arg Asn
785                 790                 795                 800

Asn Ala Lys Ser Phe Arg Cys Ala Leu Leu Ser His Arg Asp Gly Ala
                805                 810                 815

Lys Val His Leu Gly Thr Arg Pro Thr Glu Lys Gln Tyr Glu Thr Leu
                820                 825                 830

Glu Asn Gln Leu Ala Phe Leu Cys Gln Gln Gly Phe Ser Leu Glu Asn
                835                 840                 845

Ala Leu Tyr Ala Leu Ser Ala Val Gly His Phe Thr Leu Gly Cys Val
850                 855                 860

Leu Glu Asp Gln Glu His Gln Val Ala Lys Glu Glu Arg Glu Thr Pro
865                 870                 875                 880

Thr Thr Asp Ser Met Pro Pro Leu Leu Arg Gln Ala Ile Glu Leu Phe
                885                 890                 895

Asp His Gln Gly Ala Glu Pro Ala Phe Leu Phe Gly Leu Glu Leu Ile
                900                 905                 910

Ile Cys Gly Leu Glu Lys Gln Leu Lys Cys Glu Ser Gly Ser
                915                 920                 925
```

SIGNALLING SYSTEM

FIELD OF THE INVENTION

The present invention relates to a chimeric antigen receptor signalling system.

BACKGROUND TO THE INVENTION

Traditionally, antigen-specific T-cells have been generated by selective expansion of peripheral blood T-cells natively specific for the target antigen. However, it is difficult and quite often impossible to select and expand large numbers of T-cells specific for most cancer antigens. Gene-therapy with integrating vectors affords a solution to this problem as transgenic expression of Chimeric Antigen Receptor (CAR) allows generation of large numbers of T cells specific to any surface antigen by ex vivo viral vector transduction of a bulk population of peripheral blood T-cells.

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common forms of these molecules are fusions of single-chain variable fragments (scFv) derived from monoclonal antibodies which recognize a target antigen, fused via a spacer and a trans-membrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

A number of toxicities have been reported from CAR studies, and additional theoretical toxicities exist. Such toxicities include immunological toxicity caused by sustained intense activation of the CAR T-cells resulting in a macrophage activation syndrome (MAS) and "On-target off-tumour" toxicity i.e. recognition of the target antigen on normal tissues.

MAS is presumed to be caused by persistent antigen-driven activation and proliferation of T-cells which in turn release copious inflammatory cytokines leading to hyper-activation of macrophages and a feed-forward cycle of immune activation. A large spike in serum IL-6 is characteristic and the syndrome can result in a severe systemic illness requiring ICU admission.

On-target off-tumour toxicity has been reported with other CARs, for example a group of patients treated with a CAR against the renal cell carcinoma antigen CAIX developed unexpected and treatment limiting biliary toxicity. Two fatalities have been reported with CAR studies: one patient died of a respiratory distress syndrome which occurred immediately post-infusion of a large dose of 3rd generation anti-ERBB2 CAR T-cells; a further patient died in a different study after a possible cytokine storm following treatment of CLL with a second generation anti-CD19 CAR.

These toxicities are very difficult to predict even with detailed animal studies or non-human primate work. Crucially, unlike small molecules and biologics, CAR T-cells do not have a half-life and one cannot cease administration and wait for the agent to breakdown/become excreted. CAR T-cells are autonomous and can engraft and proliferate. Toxicity can therefore be progressive and fulminant.

Suicide genes are genetically expressed elements which can conditionally destroy cells which express them. Examples include Herpes-simplex virus thymidine kinase, which renders cells susceptible to Ganciclovir; inducible Caspase 9, which renders cells susceptible to a small molecular homodimerizer and CD20 and RQR8, which renders cells susceptible to Rituximab.

This technology adds a certain amount of safety to CAR T-cell therapy, however there are limitations. Firstly, it is a binary approach wherein all the CAR T-cells are destroyed upon addition of the suicide agent. In addition, medicinal therapeutics often have a therapeutic window. With a suicide gene the potency of the product cannot be tuned such that efficacy with tolerable toxicity can be achieved. Secondly, it is not clear whether a suicide gene would help with some of the immune-toxicities described above: for instance by the time a macrophage activation syndrome had been triggered, it may well no longer need the CAR T-cells to perpetuate and the suicide gene would no longer be helpful. The more acute cytokine release syndromes probably occur too quickly for the suicide gene to work. PCT/GB2015/052494 describes a CAR system which comprises separate antigen-recognition and signalling components. In this system, signalling can be rapidly inhibited/terminated despite continued binding of antigen to an antigen-recognition component of the CAR system. This inhibition of signalling occurs in the presence of an agent, such as a small molecule, which inhibits the co-localisation and interaction which would otherwise occur between the extracellular antigen-binding component and the intracellular signalling component of the CAR.

In particular, PCT/GB2015/052494 describes a CAR system which comprises;
(i) a receptor component comprising an antigen binding domain, a transmembrane domain and a first binding domain which comprises a tetracycline repressor protein (TetR); and
(ii) an intracellular signalling component comprising a signalling domain and a second binding domain which comprises a TetR interacting peptide (TiP) which specifically binds TetR of the receptor component.

The Tet operon is a well-known biological operon which has been adapted for use in mammalian cells. The TetR binds tetracycline as a homodimer and undergoes a conformational change which then modulates the DNA binding of the TetR molecules. Klotzsche et al. 2007 (J. Biol. Chem. 280, 24591-24599 (2005); Luckner et al.; J. Mol. Biol. 368, 780-790), described a phage-display derived peptide which activates the TetR. This protein (TetR interacting protein/TiP) has a binding site in TetR which overlaps, but is not identical to, the tetracycline binding site (Luckner et al.; as above). Thus TiP and tetracycline compete for binding of TetR.

In the TetR/TiP CAR system described in PCT/GB2015/052494, binding of the TetR on the receptor component and TiP on the intracellular signalling component is disrupted by the presence of tetracycline, such that in the absence of tetracycline the receptor component and the signalling component heterodimerize and binding of the antigen binding domain to antigen results in signalling through the signalling domain, whereas in the presence of tetracycline the receptor component and the signalling component do not heterodimerize and binding of the antigen binding domain to antigen does not result in signalling through the signalling domain.

Thus, in the system described in PCT/GB2015/052494, the activity of CAR-expressing cells in a patient can be dimmed or turned-off using a small-molecule agent (tetracycline), without eliminating the CAR-expressing cells from the patient.

A possible drawback of a TetR/TiP based CAR signalling system is that, because TetR is a prokaryotic protein, it may be immunogenic when expressed on a cell which is introduced to a patient.

DESCRIPTION OF THE FIGURES

FIG. 2—Structures of TetR and TiP. (a) sequence of TiP attached at the amino-terminus of an arbitrary protein; (b) Crystallography derived structure of TiP interacting with TetR (from PDB 2NS8 and Luckner et al (J. Mol. Biol. 368, 780-790 (2007)). TiP can be seen engaged deep within the TetR homodimer associating with many of the residues tetracycline associates with.

FIG. 16A—A construct for the studies described in Examples 7 and 8 which comprises nucleic acid sequences encoding a suicide gene (RQR8); a signalling component with a CD19-specific antigen binding domain (scFv) and a single binding domain (dAb) which binds the hapten (methotrexate for Example 7 and caffeine for Example 8); and an intracellular signalling component comprising a dAb interacting peptide and CD3 zeta. A sequence encoding a self-cleaving peptide (FMD-2A) was incorporated between each nucleic acid so that the three polypeptides were co-expressed.

FIG. 16B—The CAR system used in the studies described in Examples 7 and 8. The CAR system comprises a signalling component with a CD19-specific antigen binding domain (aCD19), a spacer domain, a transmembrane domain and s single binding domain (dAb) which binds the hapten (e.g. methotrexate for Example 7 and caffeine for Example 8). The CAR system also comprises an intracellular signalling component comprising a dAb interacting peptide and CD3 zeta. Addition of the hapten (methotrexate for Example 7 and caffeine for Example 8) disrupts heterodimerization between the receptor component and the intracellular signalling component so that the CAR system is no longer functional and ligation of CD19 by the antigen-binding domain does not lead to signalling through the signalling domain.

SUMMARY OF ASPECTS OF THE INVENTION

Figure 1:
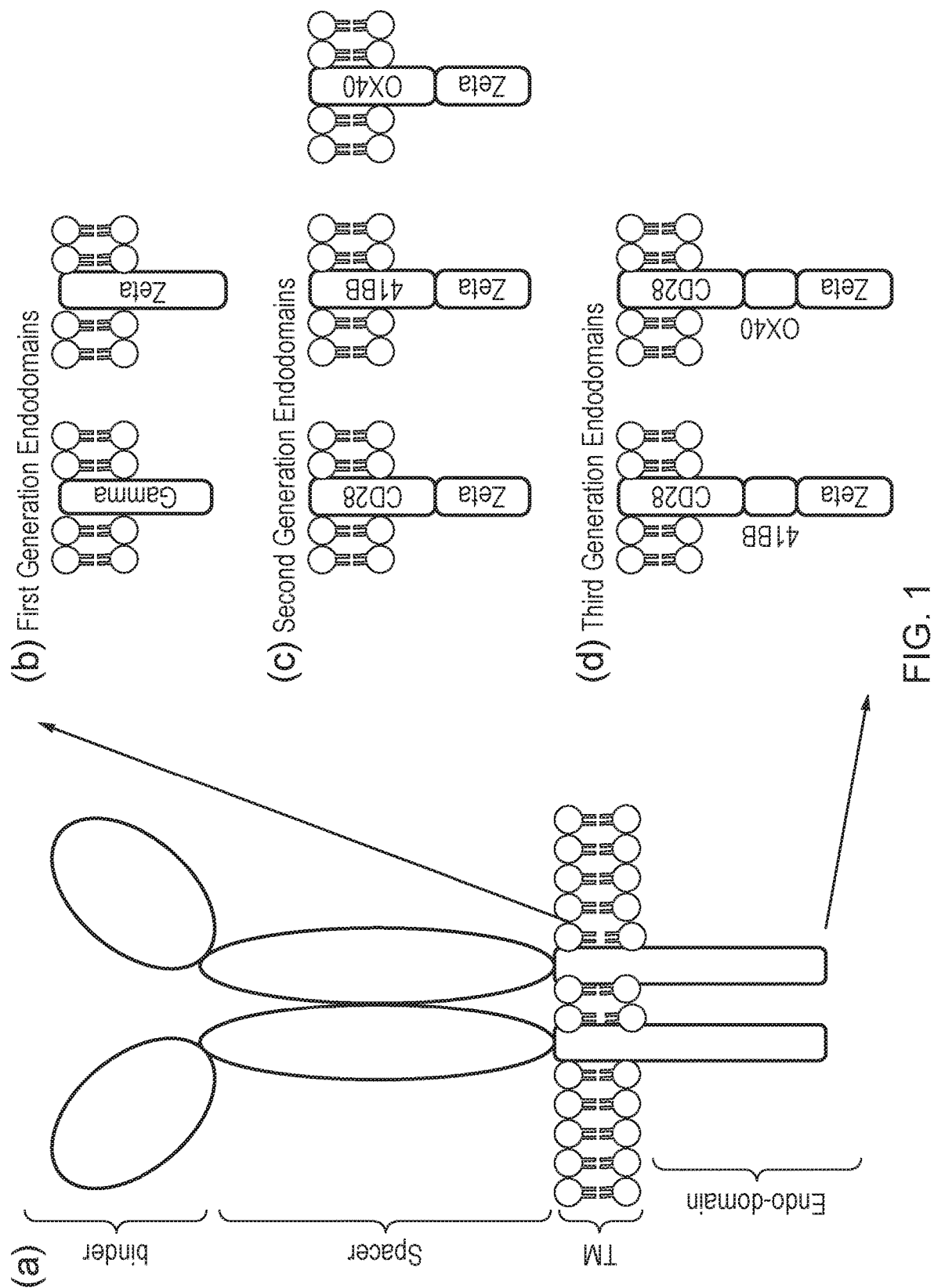
FIG. 1—a) Schematic diagram illustrating a classical CAR. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in the same compound endodomain.
Figure 2:
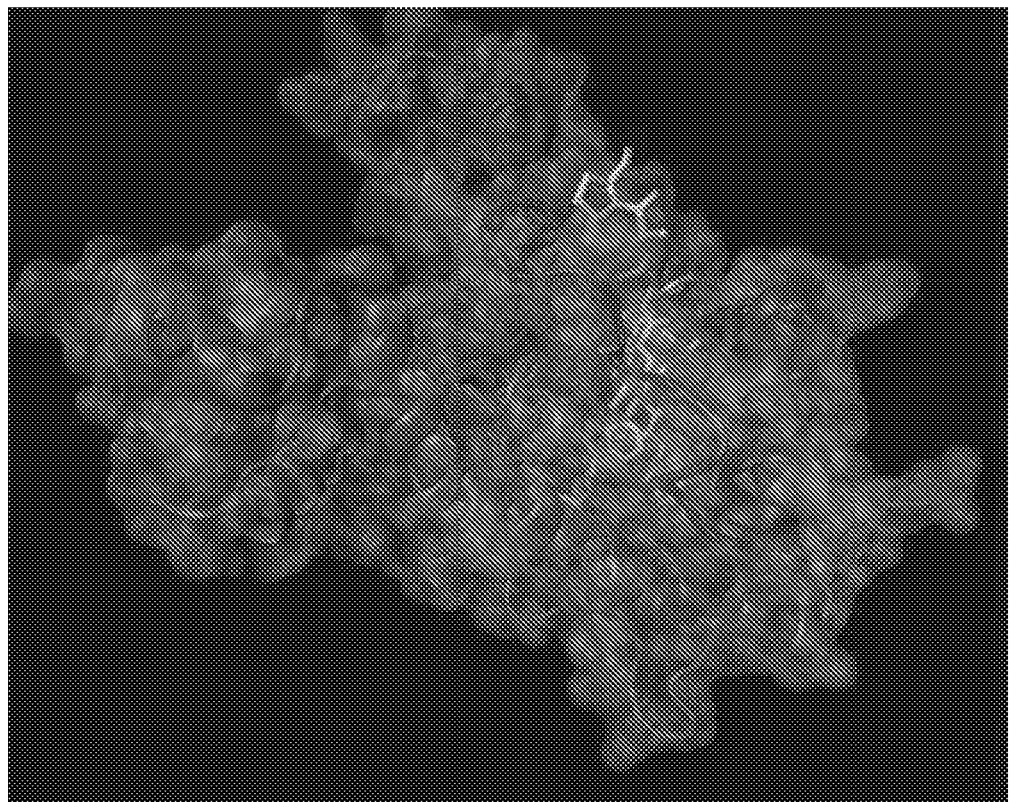

The present inventors have developed a new CAR signalling system in which interaction between the receptor component and intracellular signalling component is disrupted by the presence of an agent. In this system, heterodimerisation occurs via the binding of a single domain binder to a binding domain on the other component. The single domain binder also binds the agent, so that in the presence of agent the receptor component and intracellular signalling component disassociate and signalling cannot occur.

Thus in a first aspect the present invention provides a chimeric antigen receptor (CAR) system comprising;
(i) a receptor component comprising an antigen binding domain, a transmembrane domain and first binding domain which comprises a single domain binder which binds an agent; and
(ii) an intracellular signalling component comprising a signalling domain and a second binding domain which binds the single domain binder of the first binding domain of the receptor component;
wherein, binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain.

The single domain binder may alternatively be positioned on the intracellular signalling component, thus is a second embodiment of the first aspect of the invention there is provided a chimeric antigen receptor (CAR) system comprising;
(ii) an intracellular signalling component comprising a signalling domain and a first binding domain comprises a single domain binder;
(i) a receptor component comprising an antigen binding domain, a transmembrane domain and second binding domain which binds the single domain binder of the intracellular signalling component; and
wherein, binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain.

It is also possible for the single domain binder to be positioned on the extracellular side of the cell membrane, meaning that two further configurations are possible: one with the single binding domain on the extracellular side of the receptor component and one with the single binding domain on the extracellular side of a transmembrane domain-containing signalling component.

Thus in a third embodiment of the first aspect of the invention there is provided a chimeric antigen receptor (CAR) system comprising;
(i) a receptor component comprising an antigen binding domain, a first binding domain which comprises a single domain binder which binds an agent, and a transmembrane domain; and
(ii) a signalling component comprising a second binding domain which binds the single domain binder of the first binding domain of the receptor component, a transmembrane domain and an intracellular signalling domain and;
wherein, binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain.

In a fourth embodiment of the first aspect of the invention there is provided a chimeric antigen receptor (CAR) system comprising;
(ii) a signalling component comprising a first binding domain comprises a single domain binder, a transmembrane domain, and an intracellular signalling domain and;
(i) a receptor component comprising an antigen binding domain, a second binding domain which binds the single domain binder of the signalling component, and a transmembrane domain
wherein, binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain.

The agent may be a small molecule such as: a steroid, caffeine, cocaine or an antibiotic.

The agent may, for example, be an antibiotic such as tetracycline, doxycycline or minocycline.

The single domain binder may be or comprise: a nanobody, an affibody, a fibronectin artificial antibody scaffold, an anticalin, an affilin, a DARPin, a VNAR, an iBody, an affimer, a fynomer, a domain antibody (DAb), an abdurin/nanoantibody, a centyrin, an alphabody or a nanofitin.

The single domain binder may be or comprise a domain antibody (dAb), such as a VH or VL dAb.

The second binding domain may be or comprise a peptide which binds to the single domain binder of the first binding domain, which binding is competitively inhibited by the agent. The peptide may be identified as having the required binding affinities by for example peptide array or phage display using the single domain binder. The peptide may be eluted by adding the particular agent.

The signalling domain of the signalling component may comprise one or more of the following endodomain(s): CD3 zeta endodomain, CD28 endodomain, 41 BB endodomain and OX40 endodomain.

In a second aspect, the present invention provides a nucleic acid sequence encoding a CAR signalling system according to the first aspect of the invention, wherein the receptor component and signalling component are co-expressed by means of a self-cleaving peptide which is cleaved between the receptor component and the signalling component after translation.

In a third aspect there is provided a vector comprising a nucleic acid sequence according to the second aspect of the invention.

The vector may, for example, be a retroviral vector or a lentiviral vector or a transposon.

In a fourth aspect there is provided a cell which expresses a receptor component and a signalling component as defined in the first aspect of the invention.

The cell according may comprise a nucleic acid according to the second aspect of the invention or a vector according to the third aspect of the invention.

The cell may be an immune cell such as a T cell or an NK cell.

In a fifth aspect, there is provided a pharmaceutical composition comprising a plurality of cells according to the fourth aspect of the invention.

In a sixth aspect there is provided a pharmaceutical composition according to the fifth aspect of the invention for use in treating and/or preventing a disease.

In a seventh aspect, there is provided a method for treating and/or preventing a disease, which comprises the step of administering a pharmaceutical composition according to the fifth aspect of the invention to a subject.

The method may comprise the following steps:
(i) isolation of a cell containing sample from a subject;
(ii) transduction or transfection of the cell sample with a nucleic acid sequence according the second aspect of the invention or a vector according to the third aspect of the invention; and
(iii) administering the cells from (ii) to a subject.

The method may involve monitoring toxic activity in the subject and comprises the step of administering an agent for use in the CAR signalling system according to the first aspect of the invention to the subject to reduce adverse toxic effects.

The method may involve monitoring the progression of disease and/or monitoring toxic activity in the subject and comprises the step of administering an agent for use in the CAR signalling system according to the first aspect of the invention to the subject to provide acceptable levels of disease progression and/or toxic activity.

In the use of a pharmaceutical composition according to the sixth aspect of the invention or the method according to the seventh aspect of the invention the disease may be cancer.

In an eighth aspect there is provided the use of a pharmaceutical composition according to the fifth aspect of the invention in the manufacture of a medicament for the treatment and/or prevention of a disease.

In a ninth aspect there is provided a kit which comprises a first nucleic acid or vector encoding a receptor component as defined in the first aspect of the invention and a second nucleic acid or vector encoding a signalling component as defined in the first aspect of the invention.

In a tenth aspect there is provided a method for making a cell according to the fourth aspect of the invention, which comprises the step of introducing a nucleic acid sequence according the second aspect of the invention, or a vector according to the second aspect of the invention, or a kit according to the ninth aspect of the invention into a cell.

The cell may be from a sample isolated from a subject.

In an eleventh aspect there is provided a method for inhibiting a CAR signalling system according to the first aspect of the invention in a subject which comprises a cell according to the fourth aspect of the invention which method comprises the step of administering the agent to the subject.

The present invention therefore provides a CAR system in which signalling can be inhibited in the presence of an agent, for example a small molecule, which prevents co-localisation of the receptor component and signalling component. This allows CAR signalling and thus the potency of CAR cells to be reversibly terminated in a controllable manner in order to avoid potential toxic effects associated with unabated CAR signalling. Further the present system also allows the potency of CAR cells to be controlled pharmacologically and tuned to an acceptable balance between achieving the desired therapeutic effect and avoiding unwanted toxicities.

The system of the invention uses a single domain binder, rather than TetR, and therefore is less likely to be immunogenic when expressed in or introduced to a patient than a CAR system based on TetR/TiP.

DETAILED DESCRIPTION

Chimeric Antigen Receptors (CARs)

Classical CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain may be necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41 BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

In a first aspect, the present invention relates to a CAR system in which the antigen-recognizing/antigen binding domain is provided on a first molecule (termed herein 'receptor component'), which localizes to the cell membrane. The intracellular signalling domain is provided on a second molecule (termed herein 'signalling component').

Importantly, the receptor component comprises a first binding domain and the signalling component comprises a second binding domain which specifically binds to the first binding domain of the receptor component. Thus binding of the first binding domain to the second binding domain causes heterodimerization and co-localization of the receptor component and the signalling component. When antigen binds to the antigen binding domain of the receptor component there is signalling through the signalling component.

The first or second binding domain is also capable of binding a further agent in addition to the reciprocal binding domain. The further agent may be, for example, a small molecule. The binding between the agent and the first or second binding domain is of a higher affinity than the binding between the first binding domain and the second binding domain. Thus, when the agent is present it preferentially binds to the first or second binding domain and inhibits/disrupts the heterodimerization between the receptor component and the signalling component. When antigen binds to the antigen binding domain of the receptor component in the presence of the further agent there is no signalling through the signalling component.

Specifically, in the presence of the agent, the receptor component and signalling component are located in a stochastically dispersed manner and binding of antigen by the antigen-binding domain of the receptor component does not result in signalling through the signaling component.

Herein 'co-localization' or 'heterodimerization' of the receptor and signalling components is analogous to ligation/recruitment of the signalling component to the receptor component via binding of the first binding domain of the receptor component and the second binding domain of the signalling component.

Antigen binding by the receptor component in the presence of the agent may be termed as resulting in 'non-productive' signalling through the signalling component. Such signalling does not result in cell activation, for example T cell activation. Antigen binding by the receptor component in the absence of the agent may be termed as resulting in 'productive' signalling through the signalling component. This signalling results in T-cell activation, triggering for example target cell killing and T cell activation.

Antigen binding by the receptor component in the absence of the agent may result in signalling through the signalling component which is 2, 5, 10, 50, 100, 1,000 or 10,000-fold higher than the signalling which occurs when antigen is bound by the receptor component in the presence of the agent.

Signalling through the signalling component may be determined by a variety of methods known in the art. Such methods include assaying signal transduction, for example assaying levels of specific protein tyrosine kinases (PTKs), breakdown of phosphatidylinositol 4,5-biphosphate ($PIP_2$), activation of protein kinase C (PKC) and elevation of intracellular calcium ion concentration. Functional readouts, such as clonal expansion of T cells, upregulation of activation markers on the cell surface, differentiation into effector cells and induction of cytotoxicity or cytokine secretion may also be utilised. As an illustration, in the present examples the inventors determined levels of interleukin-2 (IL-2) produced by T-cells expressing a receptor component and signalling component of the CAR system according to the present invention upon binding of antigen to the receptor component in the presence of varying concentrations of an agent.

First Binding Domain, Second Binding Domain and Agent

The first binding domain and second binding domain of the CAR signalling system enable the selective co-localization and dimerization of the receptor component and signalling component in the absence of the agent. Thus, the first binding domain and second binding domain are capable of specifically binding.

The signalling system of the present invention is not limited by the arrangement of a specific dimerization system. The receptor component may comprise either the first binding domain or the second binding domain of a given dimerization system so long as the signalling component comprises the corresponding, complementary binding domain which enables the receptor component and signalling component to co-localize in the absence of the agent.

The first binding domain and second binding domain may be or comprise a single domain binder and a single domain binder interacting peptide respectively; or vice versa.

The agent is a molecule, for example a small molecule, which is capable of specifically binding to the first binding domain or the second binding domain at a higher affinity than the binding between the first binding domain and the second binding domain.

For example, the agent may bind the first binding domain or the second binding domain with at least 10, 20, 50, 100, 1000 or 10000-fold greater affinity than the affinity between the first binding domain and the second binding domain.

The agent may be any pharmaceutically acceptable molecule which preferentially binds the first binding domain or the second binding domain with a higher affinity than the affinity between the first binding domain and the second binding domain.

For the first and second embodiments of the CAR system of the first aspect of the invention, the agent is capable of being delivered to the cytoplasm of a target cell and being available for intracellular binding. For the third and fourth embodiments of the CAR signalling system of the first aspect of the invention, the agent binds to the first or second binding domain extracellularly.

The agent may be capable of crossing the blood-brain barrier.

Single Domain Binder

The first or second binding domain of the CAR system of the present invention comprises a single domain binder.

A "single domain binder" is an entity which binds to an agent, such as a small molecule agent, and has a single domain. A protein domain has a compact three-dimensional structure. It may be derivable from a larger protein, but the domain itself is independently stable and folds independently.

The single domain binder may have an antibody-like binding site which binds to the agent. The single domain binder may comprise one or more complementarity determining regions (CDRs). The single domain binder may comprise three CDRs The single domain binder may lack disulphide bonds. The single domain binder may lack cysteine residues.

A conventional IgG molecule is comprised of two heavy and two light chains. Heavy chains comprise three constant domains and one variable domain (VH); light chains comprise one constant domain and one variable domain (VL). The naturally functional antigen binding unit is formed by noncovalent association of the VH and the VL domain. This association is mediated by hydrophobic framework regions. IgG can be derivatized to Fab, scFv, and single domain VH or VL binders. The single domain binder used in the CAR system of the invention may be or comprise such a single domain VH or VL binder.

Heavy chain antibodies (hcAb) are found in Camelidae, lack the light chain and the CH1 domain. They comprise a single, antigen binding domain, the VHH domain. The single domain binder used in the CAR system of the invention may be or comprise such a VHH domain or derivative thereof.

A variety of non-immunoglobulin single domain binders have also been designed and characterised, including those based on natural and synthetic protein scaffolds. For example, fibronectin-derived Adnectins/monobodies are characterized by an Ig-like β-sandwich structure, anticalins are based on the lipocalin fold, affibodies derive from protein A and comprise three α helices, and DARPins are designer proteins composed of ankyrin repeats. Each design includes randomized residues that mediate ligand binding.

The single domain binder may have a molecular weight (when considered separately from the rest of the receptor component or signalling component of less than 20 kDa. It may, for example have a molecular weight of less than or equal to approximately 15 kDa, such as between 12-15 kDa, the typical molecular weight of a single domain antibody. Single chain variable fragments, which comprise two variable domains, VH and VL) typically have a molecular weight of about 25 kDa.

The single domain binder may be less than 150 amino acids in length, for example, less than 140, 130 or 120 amino acids in length. The single domain binder may be approximately 110 amino acids in length, for example from 105-115 amino acids in length The single domain binder used in the CAR system of the invention may be a single domain antibody (sdAb, also known as a nanobody), an affibody, a fibronectin artificial antibody scaffold, an anticalin, an affilin, a DARPin, a VNAR, an iBody, an affimer, a fynomer, a domain antibody (DAb), an abdurin/nanoantibody, a centyrin, an alphabody or a nanofitin.

A single-domain antibody is an antibody fragment consisting of a single monomeric variable antibody domain. The first single-domain antibodies were engineered from heavy-chain antibodies found in camelids; i.e. VHH fragments. Cartilaginous fishes also have heavy-chain antibodies (Ig-NAR, 'immunoglobulin new antigen receptor'), from which single-domain antibodies called VNAR fragments can be obtained. An alternative approach is to split the dimeric variable domains from common immunoglobulin G (IgG) from humans or mice into monomers. Although most research into single-domain antibodies is currently based on heavy chain variable domains, Nanobodies derived from light chains have also been shown to bind specifically to target epitopes.

A single-domain antibody can be obtained by immunization of dromedaries, camels, llamas, alpacas or sharks with the desired antigen and subsequent isolation of the mRNA coding for heavy-chain antibodies. By reverse transcription and polymerase chain reaction, a gene library of single-domain antibodies may be produced. Screening techniques like phage display and ribosome display help to identify the clones binding the antigen. Alternatively, single-domain antibodies can be made from common murine or human IgG with four chains. The process is similar, comprising gene libraries from immunized or naïve donors and display techniques for identification of the most specific antigens. A problem with this approach is that the binding region of common IgG consists of two domains (VH and VL), which tend to dimerize or aggregate because of their lipophilicity.

An Affibody molecule consists of three alpha helices with 58 amino acids and has a molar mass of about 6 kDa. The original Affibody protein scaffold was designed based on the Z domain (the immunoglobulin G binding domain) of protein A. In contrast to antibodies, Affibody molecules are composed of alpha helices and lack disulfide bridges.

Affibody molecules with unique binding properties are acquired by randomization of 13 amino acids located in two alpha-helices involved in the binding activity of the parent protein domain. Lately, amino acids outside of the binding surface have been substituted in the scaffold to create a surface entirely different from the ancestral protein A domain.

Specific affibody molecules binding a desired target protein can be "fished out" from libraries of variants, using phage display.

Fibronectin artificial antibody scaffold are antibody mimics based on the scaffold of the fibronectin type III domain.

Anticalins are derived from human lipocalins, a family of naturally binding proteins. Anticalins have a size of about 180 amino acids and a mass of about 20 kDa.

Affilin proteins are structurally derived from human ubiquitin (historically also from gamma-B crystallin). Affilin proteins are constructed by modification of surface-exposed amino acids of these proteins and isolated by display techniques such as phage display and screening. Like other antibody mimetics they resemble antibodies in their affinity and specificity to antigens but not in structure, Designed ankyrin repeat proteins (DARPins) are genetically engineered antibody mimetic proteins typically exhibiting highly specific and high-affinity target protein binding. They are derived from natural ankyrin proteins, one of the most common classes of binding proteins in nature, which are responsible for diverse functions such as cell signalling, regulation and structural integrity of the cell. DARPins consist of at least three repeat motifs proteins, and usually consist of four or five. Their molecular mass is about 14 or 18 kDa (kilodaltons) for four- or five-repeat DARPins, respectively.

iBodies are modular synthetic antibody mimetics based on hydrophilic polymers.

An affimer is a small, highly stable protein engineered to display peptide loops which provide a high affinity binding surface for a specific target protein. It is a protein of low molecular weight, 12-14 kDa, derived from the cysteine protease inhibitor family of cystatins.

Fynomers are small binding proteins derived from the human Fyn SH3 domain. Fynomers can be engineered to bind to target molecules with the same affinity and specificity as antibodies.

Fynomers have neither have cysteine residues nor disulfide bonds and are approximately 7 kDa in size.

Abdurins are a new class of antibody-like scaffold derived from the engineering of a single isolated CH2 domain of human IgG. Abdurins are small (12.5 kDa) proteins which retain a portion of the native Fc receptor binding motif which binds to the neonatal Fc receptor to increase protein half-life and tumour uptake.

Centyrins are a new class of alternative scaffold protein based on a consensus fibronectin domain.

Alphabodies, also known as Cell-Penetrating Alphabodies or CPAB, are small 10 kDa antibody mimetic proteins engineered to bind to a variety of antigens. Alphabodies are different from many other antibody mimetics in their ability to reach and bind to intracellular protein targets. Their single chain alpha-helical structure is designed by computer modelling, inspired by naturally existing coiled-coil protein structures.

Affitins (or Nanofitins) are antibody mimetics structurally derived from the DNA binding protein Sac7d, found in *Sulfolobus acidocaldarius*, a microorganism belonging to the archaeal domain. By randomizing the amino acids on the binding surface of Sac7d and subjecting the resulting protein library to rounds of ribosome display, the affinity can be directed towards the target of interest.

Minocycline Single Domain Binders

The present inventors have generated a number of single domain binders which specifically bind minocycline (see Example 5 below).

The present invention also provides a single domain binder which binds minocycline.

The single domain binder may comprise one or more of the CDRs listed in Table 2 below. The single domain binder may comprise one of the CDR3 sequences listed in Table 2 below. The single domain binder may comprise one the CDR1, 2 and 3 combinations listed in Table 2 below.

In particular, the single domain binder may comprise one of the following:

a) CDR1 having the amino acid sequence GRTFSSYN (SEQ ID No. 17); CDR2 having the amino acid sequence ISWSGART (SEQ ID No. 18); and CDR3 having the amino acid sequence AAGRGWGTEAILDY (SEQ ID No. 19);

b) CDR1 having the amino acid sequence GRSLSSYV (SEQ ID No. 20); CDR2 having the amino acid sequence ISWSGART (SEQ ID No. 18); and CDR3 having the amino acid sequence AAGRGWGTEAILDY (SEQ ID No. 19);

c) CDR1 having the amino acid sequence GRTFSSYN (SEQ ID No. 17); CDR2 having the amino acid sequence ISWSGART (SEQ ID No. 18); and CDR3 having the amino acid sequence VAGRGWGTEAILDY (SEQ ID No. 21);

d) CDR1 having the amino acid sequence GRTFSNYN (SEQ ID No. 22); CDR2 having the amino acid sequence INWSGGRT (SEQ ID No. 23); and CDR3 having the amino acid sequence AAGRGWGTEAILDY (SEQ ID No. 19);

e) CDR1 having the amino acid sequence GRTFSRYN (SEQ ID No. 24); CDR2 having the amino acid sequence ISWSGART (SEQ ID No. 18); and CDR3 having the amino acid sequence AAGRGWGTEAILDY (SEQ ID No. 19);

f) CDR1 having the amino acid sequence GRTFSSYN (SEQ ID No. 17); CDR2 having the amino acid sequence ISRSGGIT (SEQ ID No. 25); and CDR3 having the amino acid sequence AAGRGWGVEAILDY (SEQ ID No. 26);

g) CDR1 having the amino acid sequence GNIGLVSV (SEQ ID No. 27); CDR2 having the amino acid sequence ITGGGST (SEQ ID No. 28); and CDR3 having the amino acid sequence RLVNNGRPF (SEQ ID No. 29); or h) CDR1 having the amino acid sequence GRLSLSSYV (SEQ ID No. 30); CDR2 having the amino acid sequence ISWSGART (SEQ ID No. 18); and CDR3 having the amino acid sequence AAGRGWGTEAILDY (SEQ ID No. 19).

It may be possible to introduce one or more mutations (substitutions, additions or deletions) into the or each CDR without negatively affecting minocycline-binding activity. One, two or each CDR may, for example, have no, one, two or three amino acid mutations.

The present invention also provides a receptor component for use in a CAR system according to the present invention which comprises an antigen binding domain, a transmembrane domain and first binding domain which comprises a single domain binder as defined above which binds minocycline.

The present invention also provides an intracellular signalling component for use in a CAR system according to the present invention comprising a signalling domain and a second binding domain which binds which comprises a single domain binder as defined above which binds minocycline.

The present invention also provides a CAR system comprising a receptor component or an intracellular signalling component as defined above.

The present invention also provides a nucleic acid sequence encoding a single domain binder, a receptor component or an intracellular signalling component as defined above.

The present invention also provides a vector comprising such a nucleic acid sequence according, which may for example be a retroviral vector or a lentiviral vector or a transposon.

The present invention also provides a cell which expresses a receptor component or an intracellular signalling component as defined above.

The present invention also provides a cell which comprises a nucleic acid as above. The cell may, for example be a T cell or an NK cell.

The present invention also provides a pharmaceutical composition comprising a plurality of such cells.

The present invention also provides a method for treating and/or preventing a disease, which comprises the step of administering such a pharmaceutical composition to a subject.

The present invention also provides a method for inhibiting a CAR signalling system as defined above in a subject which method comprises the step of administering minocycline to the subject.

Caffeine Single Domain Binders

The present inventors have generated a single domain binder which specifically binds caffeine (see Example 8 below).

The present invention also provides a single domain binder which binds caffeine.

The single domain binder may comprise one or more of the following CDRs

```
Caffeine dAb CDR1
                                              (SEQ ID No. 31)
TIYSMA Caffeine dAb CDR2
                                              (SEQ ID No. 32)
TVGWSSGITYYMDSVKG Caffeine dAb CDR3
                                              (SEQ ID No. 33)
TRAYSVGYDY
```

For example, single domain binder may comprise CDR3 (SEQ ID No. 33)

It may be possible to introduce one or more mutations (substitutions, additions or deletions) into the or each CDR without negatively affecting caffeine-binding activity. One, two or each CDR may, for example, have no, one, two or three amino acid mutations.

The single domain binder may comprise the sequence shown as SEQ ID No. 11, or a variant thereof which retains caffeine-binding activity.

```
                                                SEQ ID No. 11
EVQLQASGGGLVQAGGSLRLSCTASGRTGTIYSMAWFRQAPGKEREFLAT
VGWSSGITYYMDSVKGRFTISRDNAKNSAYLQMNSLKPEDTAVYYCTATR
AYSVGYDYWGQGTQVTVSS
```

The single domain binder of the invention may comprise a variant of the sequence shown as SEQ ID No. 11 having at least 80, 85, 90, 95, 98 or 99% sequence identity, provided that the variant sequence retain the capacity to bind caffeine. The amino acid variation(s) may be in the framework regions and not in the CDRs.

The percentage identity between two polypeptide sequences may be readily determined by programs such as BLAST which is freely available at http://blast.ncbi.nlm.nih.gov.

The present invention also provides a receptor component for use in a CAR system according to the present invention which comprises an antigen binding domain, a transmembrane domain and first binding domain which comprises a single domain binder as defined above which binds caffeine.

The present invention also provides an intracellular signalling component for use in a CAR system according to the present invention comprising a signalling domain and a second binding domain which binds which comprises a single domain binder as defined above which binds caffeine.

The present invention also provides a CAR system comprising a receptor component or an intracellular signalling component as defined above.

The present invention also provides a nucleic acid sequence encoding a single domain binder, a receptor component or an intracellular signalling component as defined above.

The present invention also provides a vector comprising such a nucleic acid sequence according, which may for example be a retroviral vector or a lentiviral vector or a transposon.

The present invention also provides a cell which expresses a receptor component or an intracellular signalling component as defined above.

The present invention also provides a cell which comprises a nucleic acid as above. The cell may, for example be a T cell or an NK cell.

The present invention also provides a pharmaceutical composition comprising a plurality of such cells.

The present invention also provides a method for treating and/or preventing a disease, which comprises the step of administering such a pharmaceutical composition to a subject.

The present invention also provides a method for inhibiting a CAR signalling system as defined above in a subject which method comprises the step of administering caffeine to the subject.

Single Domain Binder-Interacting Peptide

In the CAR system of the present invention heterodimerisation of the receptor and signalling component may occur through the binding of the single domain binder with a single domain binder-interacting peptide (sdbiP).

The sdbiP may, for example, be between 8-30, for example 10-20 amino acids in length.

Suitable sdbiPs may be generated and identified using peptide display methods such as phage display, CIS display, ribosome display and mRNA display (Ullman et al (2011) Briefings in Functional Genomics 10:125-134).

Peptides in a phage display peptide library may be selected using techniques such as biopanning (Miura et al (2004) Biochim. Et Biophys. Acta 1673:131-138).

The agent itself may be used to elute the peptides, for example in a peptide array, so that the selection method reflects the properties of the sdbiP in the CAR signalling system, namely that it binds the single domain binder, but the binding is competitively inhibited by the presence of the agent.

Once identified, the sdbiP may be incorporated into the receptor molecule (first and third embodiments) or the signalling molecule (second and fourth embodiments) and tested to make sure the binding properties of the sdbiP are retained.

Single Domain Binder-Interacting Peptide to Methotrexate Single Domain Binder

The present inventors have generated a number of sdbiP which specifically bind a methotraxate dAb (see Example 7 below).

The present invention also provides an sdbiP which binds a methotrexate dAb.

The sdbiP may comprise of consist of one of the amino acid sequences shown as SEQ ID No. 6 to 10.

```
                                                 SEQ ID No. 6
ACNAGHLSQC

SEQ ID No. 7
ASLAITH

SEQ ID No. 8
ACISLTLNRC

SEQ ID No. 9
QTEKNPL

SEQ ID No. 10
ACNAGHLSQC
```

The present invention also provides a receptor component for use in a CAR system according to the present invention which comprises an antigen binding domain, a transmembrane domain and first binding domain which comprises an sdbiP as defined above which binds a methotrexate dAb.

The present invention also provides an intracellular signalling component for use in a CAR system according to the present invention comprising a signalling domain and a second binding domain which binds which comprises an sdbiP as defined above which binds a methotrexate dAb.

The present invention also provides a CAR system comprising a receptor component or an intracellular signalling component as defined above.

The present invention also provides a nucleic acid sequence encoding a single domain binder, a receptor component or an intracellular signalling component as defined above.

The present invention also provides a vector comprising such a nucleic acid sequence according, which may for example be a retroviral vector or a lentiviral vector or a transposon.

The present invention also provides a cell which expresses a receptor component or an intracellular signalling component as defined above.

The present invention also provides a cell which comprises a nucleic acid as above. The cell may, for example be a T cell or an NK cell.

The present invention also provides a pharmaceutical composition comprising a plurality of such cells.

The present invention also provides a method for treating and/or preventing a disease, which comprises the step of administering such a pharmaceutical composition to a subject.

The present invention also provides a method for inhibiting a CAR signalling system as defined above in a subject which method comprises the step of administering methotrexate to the subject.

Single Domain Binder-Interacting Peptide to Caffeine Single Domain Binder

The present inventors have generated a number of sdbiP which specifically bind a caffeine dAb (see Example 8 below).

The present invention also provides an sdbiP which binds a caffeine dAb.

The sdbiP may comprise of consist of one of the amino acid sequences shown as SEQ ID No. 12 to 16.

```
                                   SEQ ID No. 12
HTLNKPP

SEQ ID No. 13
DLSIGNH

SEQ ID No. 14
HDSPTAA

SEQ ID No. 15
YPDVPLA

SEQ ID No. 16
ACTYLNSAKC
```

The present invention also provides a receptor component for use in a CAR system according to the present invention which comprises an antigen binding domain, a transmembrane domain and first binding domain which comprises an sdbiP as defined above which binds a caffeine dAb.

The present invention also provides an intracellular signalling component for use in a CAR system according to the present invention comprising a signalling domain and a second binding domain which binds which comprises an sdbiP as defined above which binds a caffeine dAb.

The present invention also provides a CAR system comprising a receptor component or an intracellular signalling component as defined above.

The present invention also provides a nucleic acid sequence encoding a single domain binder, a receptor component or an intracellular signalling component as defined above.

The present invention also provides a vector comprising such a nucleic acid sequence according, which may for example be a retroviral vector or a lentiviral vector or a transposon.

The present invention also provides a cell which expresses a receptor component or an intracellular signalling component as defined above.

The present invention also provides a cell which comprises a nucleic acid as above. The cell may, for example be a T cell or an NK cell.

The present invention also provides a pharmaceutical composition comprising a plurality of such cells.

The present invention also provides a method for treating and/or preventing a disease, which comprises the step of administering such a pharmaceutical composition to a subject.

The present invention also provides a method for inhibiting a CAR signalling system as defined above in a subject which method comprises the step of administering caffeine to the subject.

Agent

The agent may be a small molecule such as: a steroid, methotrexate, caffeine, cocaine or an antibiotic.

A steroid is an organic compound with four "fused" carbon rings. Examples of steroids include the dietary lipid cholesterol, the sex hormones estradiol and testosterone and the anti-inflammatory drug dexamethasone.

The steroid core structure is composed of seventeen carbon atoms, bonded in four "fused" rings: three six-member cyclohexane rings (rings A, B and C in the first illustration) and one five-member cyclopentane ring (the D ring). Steroids vary by the functional groups attached to this four-ring core and by the oxidation state of the rings. Sterols are forms of steroids with a hydroxyl group at position three and a skeleton derived from cholestane.

Methotrexate (MTX), formerly known as amethopterin, is an antimetabolite and antifolate drug.

Caffeine is a purine, a methylxanthine alkaloid. It is a stimulant of the central nervous system, but is generally recognised as safe (GRAS) by the Food and Dru Administration. Toxic doses, over 10 grams per day for an adult, are much higher than typical dose of under 500 milligrams per day. A cup of coffee contains 80-175 mg of caffeine.

Cocaine, also known as benzoylmethylecgonine or coke, is a strong stimulant. Various analogs of cocaine (methyl (1R,2R,3S,5S)-3-(benzoyloxy)-8-methyl-8-azabicyclo [3.2.1]octane-2-carboxylate) are known including stereoisomers; 3β-phenyl ring substituted analogues; 2β-substituted analogues; N-modified analogues of cocaine; 3β-carbamoyl analogues; 3β-alkyl-3-benzyl tropanes; 6/7-substituted cocaines; 6-alkyl-3-benzyl tropanes; and piperidine homologues.

Antibiotics or antibacterials are a type of antimicrobial used in the treatment and prevention of bacterial infection. Antibacterial antibiotics are commonly classified based on their mechanism of action, chemical structure, or spectrum of activity. Most target bacterial functions or growth processes. Those that target the bacterial cell wall (penicillins and cephalosporins) or the cell membrane (polymyxins), or interfere with essential bacterial enzymes (rifamycins, lipiarmycins, quinolones, and sulfonamides) have bactericidal activities. Those that target protein synthesis (macrolides, lincosamides and tetracyclines) are usually bacteriostatic (with the exception of bactericidal aminoglycosides). Further categorization is based on their target specificity. "Narrow-spectrum" antibacterial antibiotics target specific types of bacteria, such as Gram-negative or Gram-positive bacteria, whereas broad-spectrum antibiotics affect a wide range of bacteria. Four new classes of antibacterial antibiotics have been brought into clinical use in the last ten years: cyclic lipopeptides (such as daptomycin), glycylcyclines (such as tigecycline), oxazolidinones (such as linezolid), and lipiarmycins (such as fidaxomicin).

The agent may, for example, be an antibiotic such as tetracycline, or a derivative thereof such as doxycycline or minocycline.

Method

The present invention also relates to a method for inhibiting the CAR system of the first aspect of the invention, which method comprises the step of administering the agent. As described above, administration of the agent results in a disruption of the co-localization between the receptor component and the signalling component, such that signalling through the signalling component is inhibited even upon binding of antigen to the antigen binding domain.

The first and second binding domains may facilitate signalling through the CAR system which is proportional to the concentration of the agent which is present. Thus, whilst the agent binds the first binding domain or the second binding domain with a higher affinity than binding affinity between the first and second binding domains, co-localization of the receptor and signalling components may not be completely ablated in the presence of low concentrations of the agent. For example, low concentrations of the agent may decrease the total level of signalling in response to antigen without completely inhibiting it. The specific concentrations of agent will differ depending on the level of signalling required and the specific binding domains and agent. Levels of signalling and the correlation with concentration of agent can be determined using methods known in the art, as described above.

Receptor Component

The present invention provides a receptor component comprising an antigen-binding domain, an optional spacer domain, a transmembrane domain and a first biding domain which comprises a single domain binder. When expressed in a cell, the receptor component localises to the cell membrane. Here, the antigen-binding domain of the molecule is orientated on the extracellular side of the membrane. The first binding domain may be localised to the intracellular or extracellular side of the membrane.

The receptor component therefore provides the antigenbinding function of the CAR system of the present invention.

Antigen Binding Domain

The antigen-binding domain is the portion of a classical CAR which recognizes antigen. In the signalling system of the present invention the antigen-binding is located within the receptor component.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

Various tumour associated antigens (TAA) are known, as shown in the following Table 1. The antigen-binding domain used in the present invention may be a domain which is capable of binding a TAA as indicated therein.

TABLE 1

| Cancer type | TAA |
|---|---|
| Diffuse Large B-cell Lymphoma | CD19, CD20 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Transmembrane Domain

The transmembrane domain is the sequence of a classical CAR that spans the membrane. In the signalling system of the present invention the transmembrane domain is located in the receptor component. It may comprise a hydrophobic alpha helix. The transmembrane domain may be derived from CD28, which gives good receptor stability.

Signal Peptide

The receptor component of the CAR system of the present invention may comprise a signal peptide so that when the receptor component is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

Spacer Domain

The CAR system described herein may comprise a spacer sequence to connect the antigen-binding domain with the transmembrane domain in the receptor component. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Receptor Component Comprising a Plurality of First Binding Domains

The receptor component may comprise a plurality of first binding domains and thus be capable of recruiting more than one signalling component.

The plurality of first binding domains may be present in a single intracellular domain of the receptor component.

The receptor component may comprise an appropriate number of transmembrane domains such that each first binding domain is orientated on the intracellular side of the cell membrane. For example the receptor component may comprise 3, 5, 7, 9, 11, or more transmembrane domains. In this way, a single receptor component may recruit multiple signalling components amplifying signalling in response to antigen.

The first binding domains may each be variants which have a different affinity for the second binding domain of the signalling component.

Multiple Receptor Components

Figure 11:
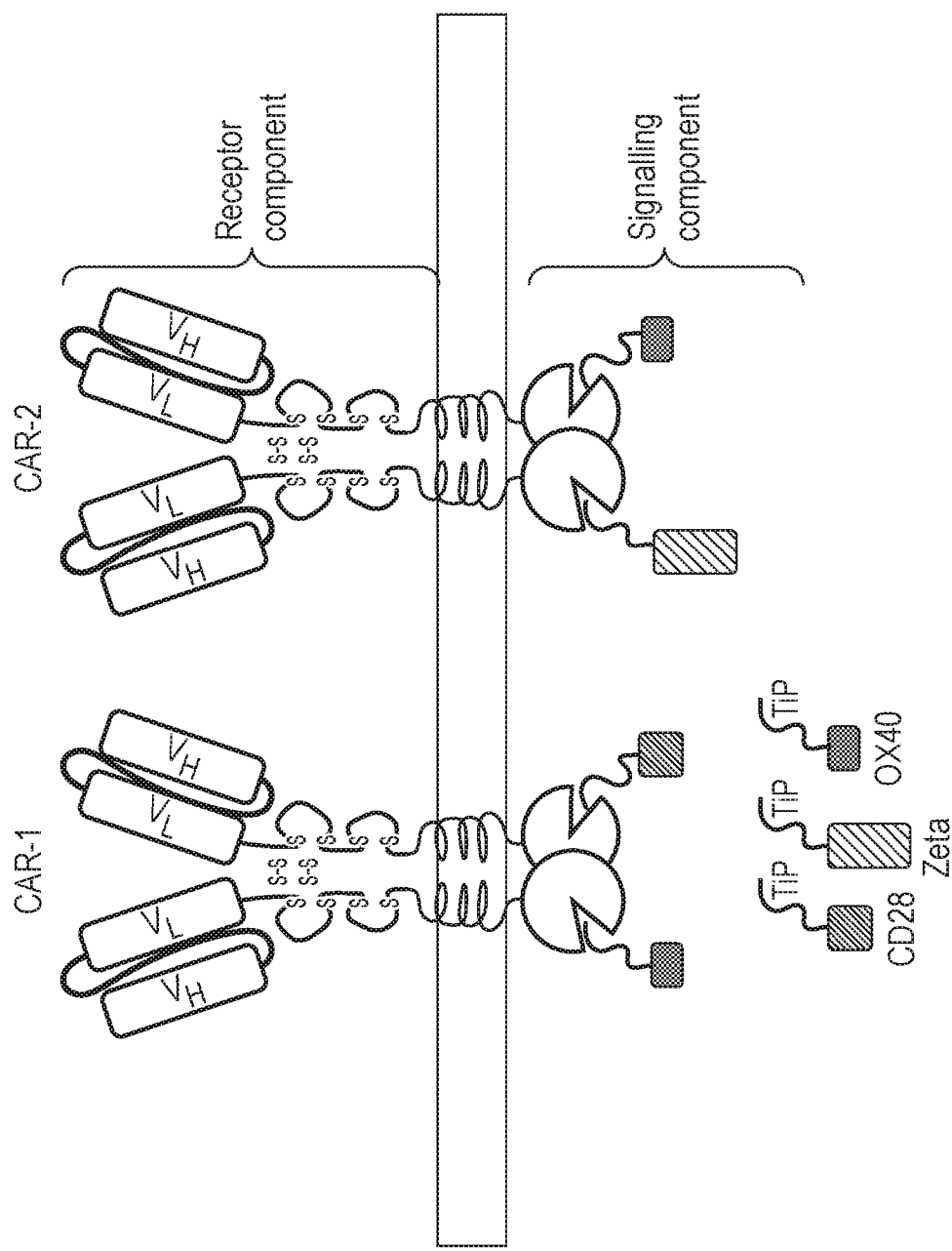
FIG. 11—A tetCAR signalling system utilising a plurality of receptor components and a plurality of signalling components, each signalling component containing a single endodomain.
Figure 12:
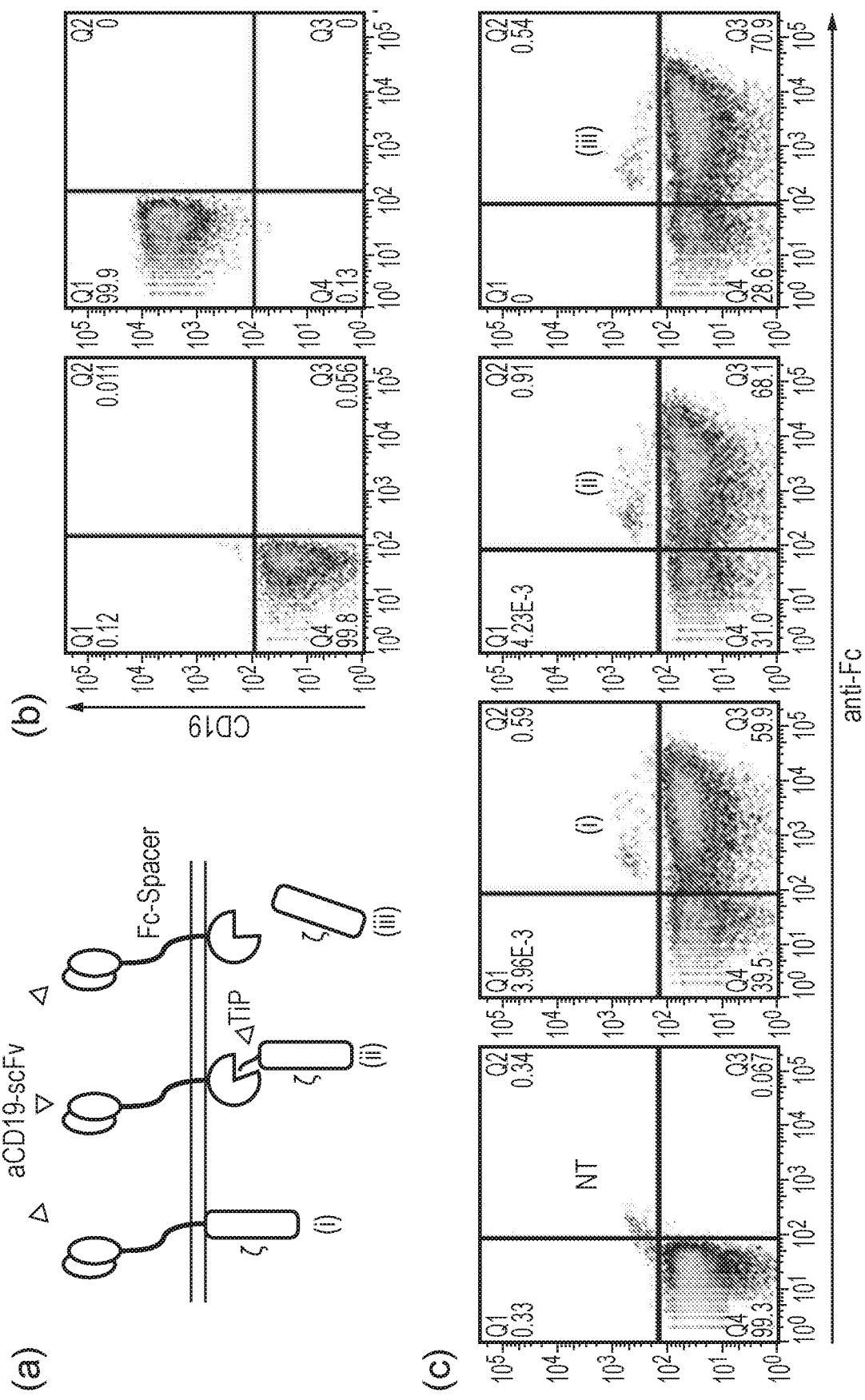
FIG. 12—TetCAR signalling in primary cells (a) Different constructs tested: (i) Classic CAR; (ii) tetCAR; (iii) control tetCAR where TiP has been deleted. (b) non-transduced and SupT1.CD19 cells stained for CD19; (c) Non-transduced T-cells and T-cells transduced with the different CAR constructs stained with anti-Fc.

In another embodiment of the invention, the CAR system may comprise two or more receptor components each recognizing different antigens but comprising of the same intracellular first binding domain. Such a CAR system would be capable of recognizing multiple antigens (FIG. 11). This might be useful for instance in avoiding tumour escape. In a further related aspect of the invention, the first binding domains of the receptor components differ in residues which dictate their affinity for the second binding domain of the signalling component. In this way, a CAR system can be tuned such that signalling in response to one antigen is greater or lesser than the response to another (FIG. 11). This might be useful for instance when targeting two tumour antigens simultaneously but one is expressed at a higher density than the other. Response to this antigen could be tuned down to avoid toxicity caused by over-stimulation.

Methods suitable for altering the amino acid residues of the first or second binding domain such that the binding affinity between the two domains is altered are known in the art and include substitution, addition and removal of amino acids using both targeted and random mutagenesis. Methods for determining the binding affinity between a first binding domain and a second binding domain are also well known in the art and include bioinformatics prediction of protein-protein interactions, affinity electrophoresis, surface plasma resonance, bio-layer interferometry, dual polarisation interferometry, static light scattering and dynamic light scattering.

Signalling Component

The present invention also provides a signalling component comprising a signalling domain and a second binding domain which comprises a single domain binder. The signalling component may be a soluble molecule which localises to the cytoplasm when it is expressed in a cell, for example a T cell (second embodiment of the first aspect of the invention). Alternatively, the signalling component may also comprise a transmembrane domain, such that it localises to the cell surface when expressed in a cell (fourth embodiment of the first aspect of the invention).

No signalling occurs through the signalling domain of the signalling component unless it is co-localised with the receptor component provided by the present invention. Such co-localisation occurs only in the absence of the agent, as described above.

Intracellular Signalling Domain

The intracellular signalling domain is the signal-transmission portion of a classical CAR. In the signalling system of the present invention the intracellular signalling domain (signalling domain) is located in the signalling component. In the absence of the agent, the membrane-bound, receptor component and the intracellular signalling component are brought into proximity. After antigen recognition, receptors cluster, native CD45 and CD148 are excluded from the synapse and a signal is transmitted to the cell.

As such the signalling domain of the signalling component is analogous to the endodomain of a classical CAR molecule.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 1B).

Figure 3:
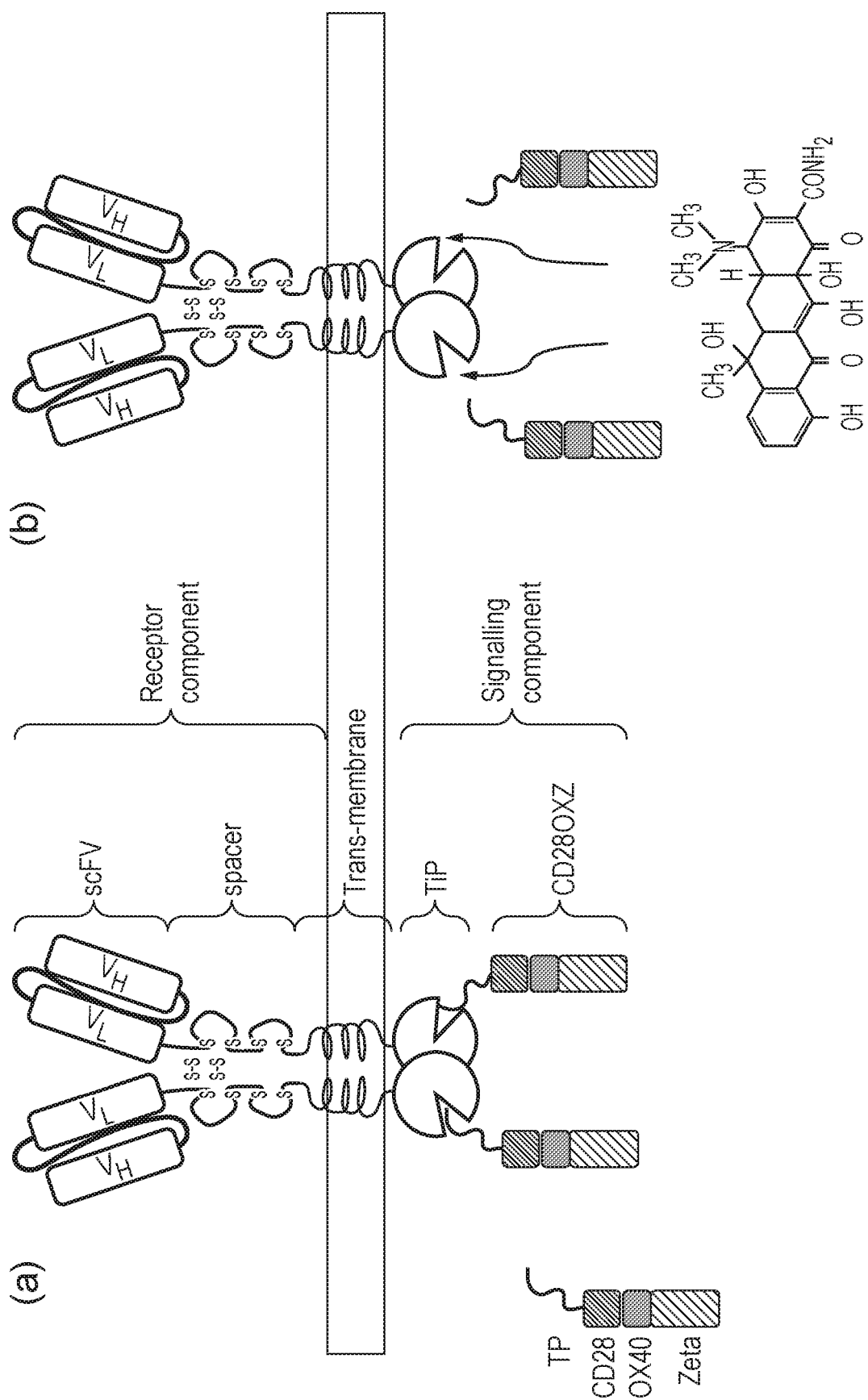
FIG. 3—A TetR/TiP based CAR signalling system (a) A membrane spanning receptor component comprises an extracellular antigen-binding domain, a transmembrane domain and an intracellular linker to TetR. A separate molecule, the signalling component, comprises an intracellular protein which is generated by fusion of TiP to one or several T-cell signalling domains. In the absence of tetracycline or tetracycline analogues, the receptor and the signalling components interact and in the presence of cognate antigen the system signals. (b) In the presence of tetracycline or tetracycline analogues, TiP is displaced from TetR and the receptor can not transmit signals even in the presence of cognate antigen.
Figure 4:
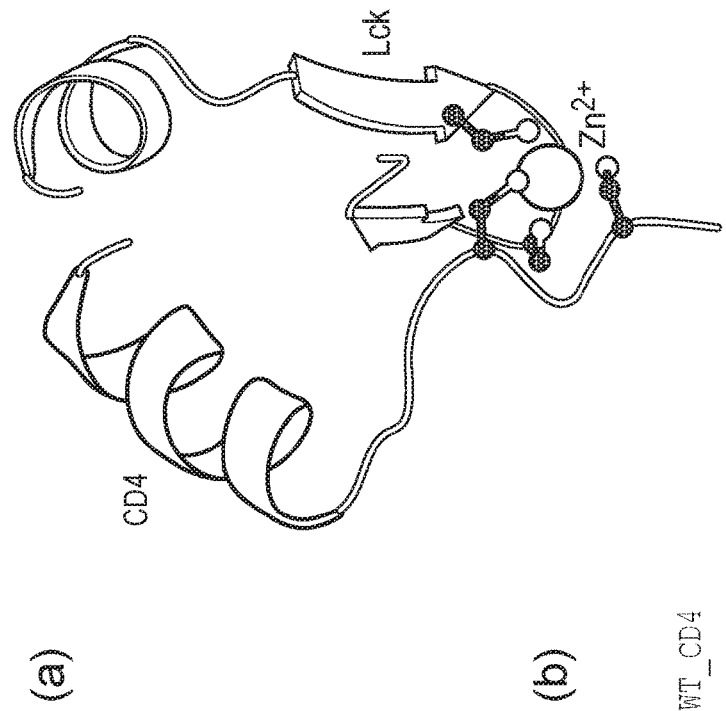
FIG. 4—Intracellular linker domain derived from CD4.

The signalling component described herein comprises a signalling domain, it may comprise the CD3-Zeta endodomain alone, the CD3-Zeta endodomain with that of either CD28 or OX40 or the CD28 endodomain and OX40 and CD3-Zeta endodomain (FIG. 3A).

The signalling component of a CAR system according to the present invention may comprise the sequence shown as SEQ ID NO: 1, 2 or 3 or a variant thereof having at least 80% sequence identity.

```
-CD3 Z endodomain
                                          SEQ ID NO: 1
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

-CD28 and CD3 Zeta endodomains
                                          SEQ ID NO: 2
SKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

-CD28, OX40 and CD3 Zeta endodomains
                                          SEQ ID NO: 3
SKRSRLLHSDYMNMTPRRPGPTRKHYQPYAPPRDFAAYRSRDQRLPPDAH

KPPGGGSFRTPIQEEQADAHSTLAKIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR
```

A variant sequence may have at least 80%, 85%, 90%, 95%, 98% or 99% sequence identity to SEQ ID NO: 1, 2 or 3, provided that the sequence provides an effective intracellular signalling domain.

Multiple Signalling Components

Figure 9:
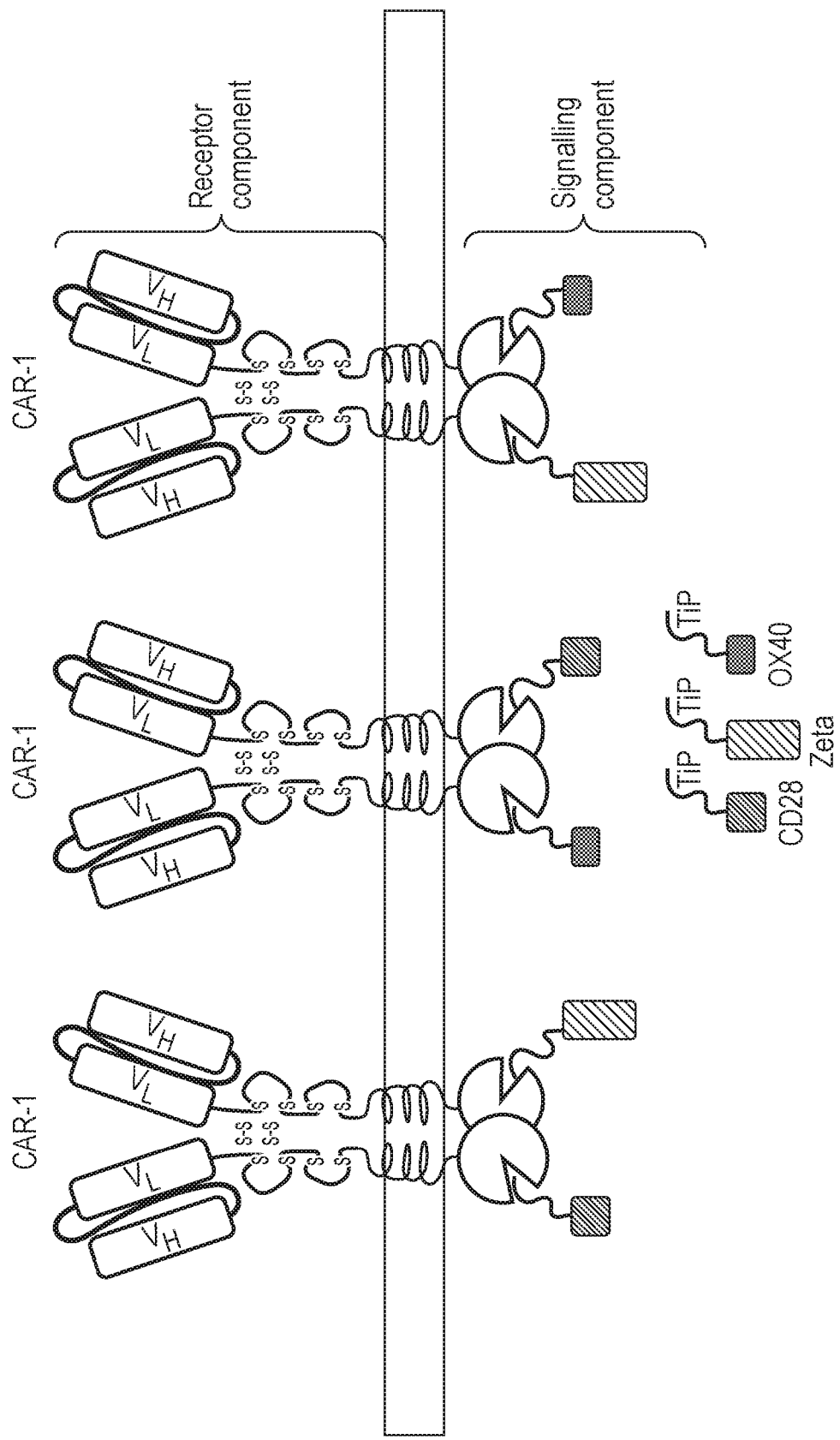
FIG. 9—A tetCAR signalling system utilising a plurality of signalling components containing single endodomains. A single CAR is expressed with many different signalling components all of which comprise TiP at their amino terminus but a different individual signalling domain, in contrast to a compound signalling domain. These randomly interact with the receptor component. Lack of steric interaction between the different signalling domains and their second messengers improves their function.

The signalling system according to the first aspect of the present invention may comprise a plurality of signalling components, each comprising a signalling domain and a second binding domain, wherein each second binding domain is bound by the same first binding domain of the receptor component but the signalling domains comprise different endodomains (FIG. 9). In this way, multiple different endodomains can be activated simultaneously. This is advantageous over a compound signalling domain since each signalling domain remains unencumbered from other signalling domains.

Figure 10:
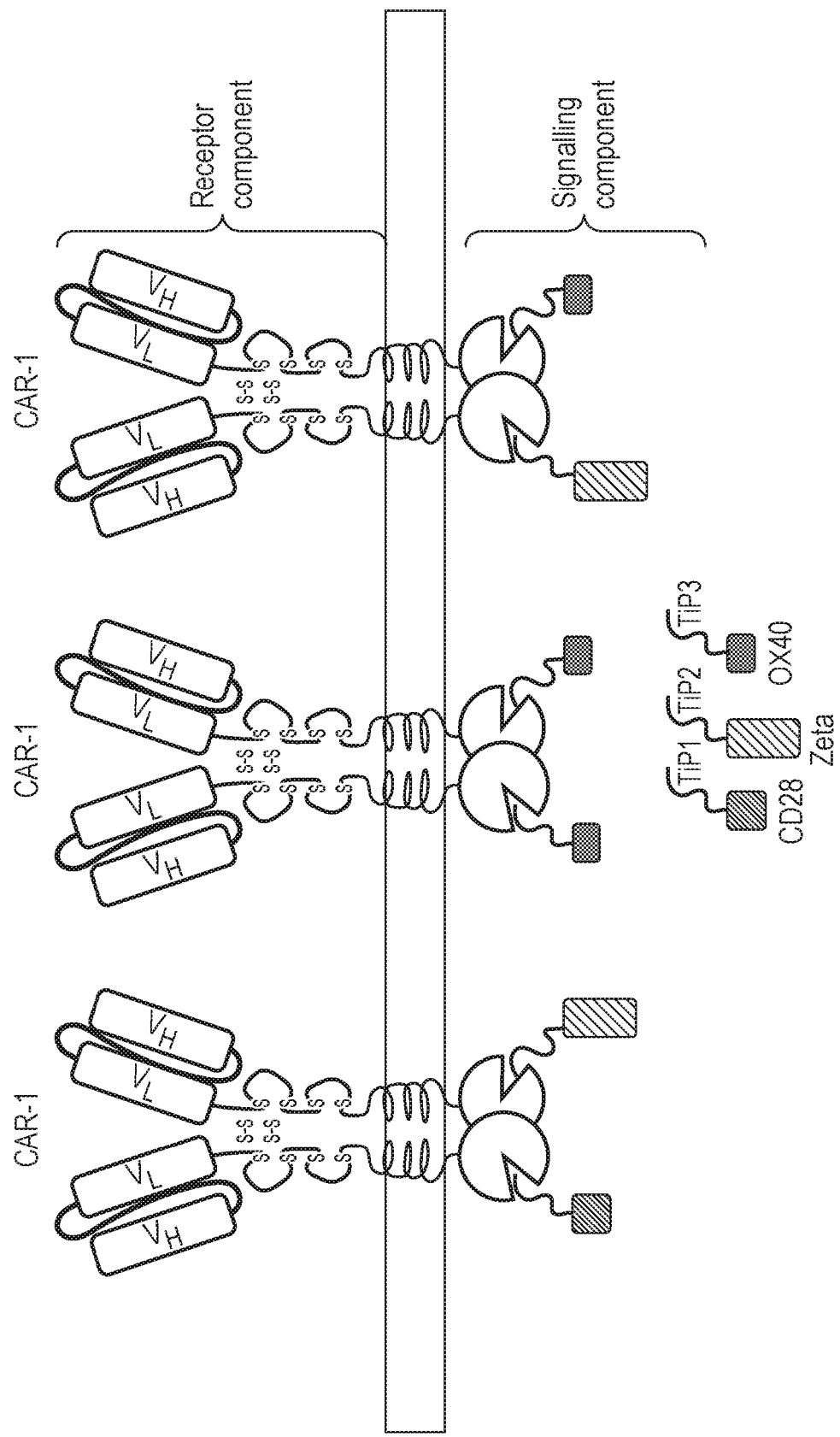
FIG. 10—A tetCAR signalling system utilising a plurality of signalling components containing single endodomains and different TiP domains. Each signalling component comprises of an individual signalling domain. Each signalling component also comprises of a TiP, however each TiP has different affinities to the TetR domain. Hence the stoichiometry of the interactions between the CAR and the signalling domains can be varied. In the example shown, the signalling system is constructed such that OX40>CD3Zeta>CD28.

If each signalling component comprises a second binding domain which differs in residues which alter their affinity to the first binding domain of the receptor component, the signalling components comprising different signalling domains ligate to the first binding domain with differing kinetics (FIG. 10). This allows greater control over the signalling in response to antigen-binding by the receptor component as different signalling components are recruited to the receptor component in varying kinetics/dynamics. This is advantageous since rather than a fixed equal ratio of signal transmitted by a compound endodomain, an optimal T-cell activation signal may require different proportions of different immunological signals.

Nucleic Acid

The present invention further provides a nucleic acid encoding the receptor component of the second aspect and a nucleic acid encoding a signalling component of the third aspect.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid of the invention may be a nucleic acid which encodes both the receptor component and the signalling component.

The nucleic acid may produce a polypeptide which comprises the receptor component and the signalling component joined by a cleavage site. The cleavage site may be self-cleaving, such that when the polypeptide is produced, it is immediately cleaved into the receptor component and the signalling component without the need for any external cleavage activity.

Various self-cleaving sites are known, including the Foot-and-Mouth disease virus (FMDV) 2a self-cleaving peptide, which has the sequence shown:

```
                                    SEQ ID NO: 4
RAEGRGSLLTCGDVEENPGP.
or
                                    SEQ ID NO: 5
QCTNYALLKLAGDVESNPGP
```

The co-expressing sequence may be an internal ribosome entry sequence (IRES). The co-expressing sequence may be an internal promoter.

The present invention also provides a kit comprising a nucleic acid encoding the receptor component of the second aspect and/or a nucleic acid encoding a signalling component of the third aspect.

Vector

The present invention also provides a vector, or kit of vectors which comprises one or more nucleic acid sequence(s) encoding a receptor component of the second aspect and/or signalling component of the third aspect of the invention. Such a vector may be used to introduce the nucleic acid sequence(s) into a host cell so that it expresses the receptor component and signalling component of the CAR system according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention also relates to an cell comprising the CAR system according to the first aspect of the invention.

The cell may comprise a nucleic acid or a vector of the present invention.

The cell may comprise a receptor component and a signalling component of the present invention.

The cell may comprise at least one signalling component of the present invention. For example the cell may comprise one, two, three, four, five, or more signalling components of the present invention.

The cell may comprise at least one receptor component of the present invention. For example the cell may comprise one, two, three, four, five, or more receptor components of the present invention.

The cell may be an immune cell, such as a cytolytic immune cell. Cytolytic immune cells can be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing the molecules of the CAR system according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing the molecules of the CAR system according to the first aspect of the invention may be derived from ex vivo differentiation of inducible progenitor cells or embryonic progenitor cells to T cells. Alternatively, an immortalized T-cell line which retains its lytic function and could act as a therapeutic may be used.

In all these embodiments, CAR cells are generated by introducing DNA or RNA coding for the receptor component and signalling component by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR system according to the first aspect of the invention, for example by treatment with an anti-CD3 monoclonal antibody.

The T or NK cell of the invention may be made by:
  (i) isolation of a T or NK cell-containing sample from a subject or other sources listed above; and
  (ii) transduction or transfection of the T or NK cells with one or more a nucleic acid sequence(s) encoding the receptor component and/or signalling component of the CAR system according to the second and third aspects of the invention.

The T or NK cells may then by purified, for example, selected on the basis of expression of the antigen-binding domain of the antigen-binding polypeptide.

The present invention also provides a kit which comprises a T or NK cell comprising the CAR system according to the first aspect of the invention.

Pharmaceutical Composition

The present invention also relates to a pharmaceutical composition containing a plurality of cells expressing the components of the CAR system of the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
  (i) isolating a T or NK cell-containing sample;
  (ii) transducing or transfecting such cells with a nucleic acid sequence or vector provided by the present invention;
  (iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The methods provided by the present invention for treating a disease may involve monitoring the progression of the disease and any toxic activity and administering an agent suitable for use in the CAR system according to the first aspect of the invention to inhibit CAR signalling and thereby reduce or lessen any adverse toxic effects.

The methods provided by the present invention for treating a disease may involve monitoring the progression of the disease and monitoring any toxic activity and adjusting the dose of the agent administered to the subject to provide acceptable levels of disease progression and toxic activity.

Monitoring the progression of the disease means to assess the symptoms associated with the disease over time to determine if they are reducing/improving or increasing/worsening.

Toxic activities relate to adverse effects caused by the CAR cells of the invention following their administration to a subject. Toxic activities may include, for example, immunological toxicity, biliary toxicity and respiratory distress syndrome.

The level of signalling through the signalling system of the first aspect of the invention, and therefore the level of activation of CAR cells expressing the signalling system, may be adjusted by altering the amount of agent present, or the amount of time the agent is present. In the present method the level of CAR cell activation may be augmented by decreasing the dose of agent administered to the subject or decreasing the frequency of its administration. Conversely, the level of CAR cell activation may be reduced by increasing the dose of the agent, or the frequency of administration to the subject.

Higher levels of CAR cell activation are likely to be associated with reduced disease progression but increased toxic activities, whilst lower levels of CAR cell activation are likely to be associated with increased disease progression but reduced toxic activities.

The present invention also provides a method for treating and/or preventing a disease in a subject which subject comprises cells of the invention, which method comprises the step of administering an agent suitable for use in the CAR system according to the first aspect to the subject. As such, this method involves administering a suitable agent to a subject which already comprises CAR cells of the present invention.

As such the dose of agent administered to a subject, or the frequency of administration, may be altered in order to provide an acceptable level of both disease progression and toxic activity. The specific level of disease progression and toxic activities determined to be 'acceptable' will vary according to the specific circumstances and should be assessed on such a basis. The present invention provides a method for altering the activation level of the CAR cells in order to achieve this appropriate level.

The agent may be administered in the form of a pharmaceutical composition. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

The present invention provides a CAR cell of the present invention for use in treating and/or preventing a disease.

The invention also relates to the use of a CAR cell of the present invention in the manufacture of a medicament for the treatment and/or prevention of a disease.

The present invention also provides an agent suitable for inhibiting a CAR system according to the first aspect of the invention for use in treating and/or preventing a disease.

The present invention also provides an agent for use in inhibiting a CAR system according to the first aspect of the invention in a CAR cell.

The invention also provides the use of an agent suitable for inhibiting a CAR system according to the first aspect of the invention in the manufacture of a medicament for the treatment and/or prevention of a disease.

The disease to be treated and/or prevented by the methods of the present invention may be an infection, such as a viral infection.

The methods of the invention may also be for the control of pathogenic immune responses, for example in autoimmune diseases, allergies and graft-vs-host rejection.

The methods may be for the treatment of a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The CAR cells of the present invention may be capable of killing target cells, such as cancer cells. The target cell may be recognisable by expression of a TAA, for example the expression of a TAA provided above in Table 1.

The CAR cells and pharmaceutical compositions of present invention may be for use in the treatment and/or prevention of the diseases described above.

The CAR cells and pharmaceutical compositions of present invention may be for use in any of the methods described above.

The invention will now be further described by way of Examples, which are meant to serve to assist one of ordinary skill in the art in carrying out the invention and are not intended in any way to limit the scope of the invention.

EXAMPLES

Example 1—Functionality of the Original TetCAR Signalling System

Figure 5:
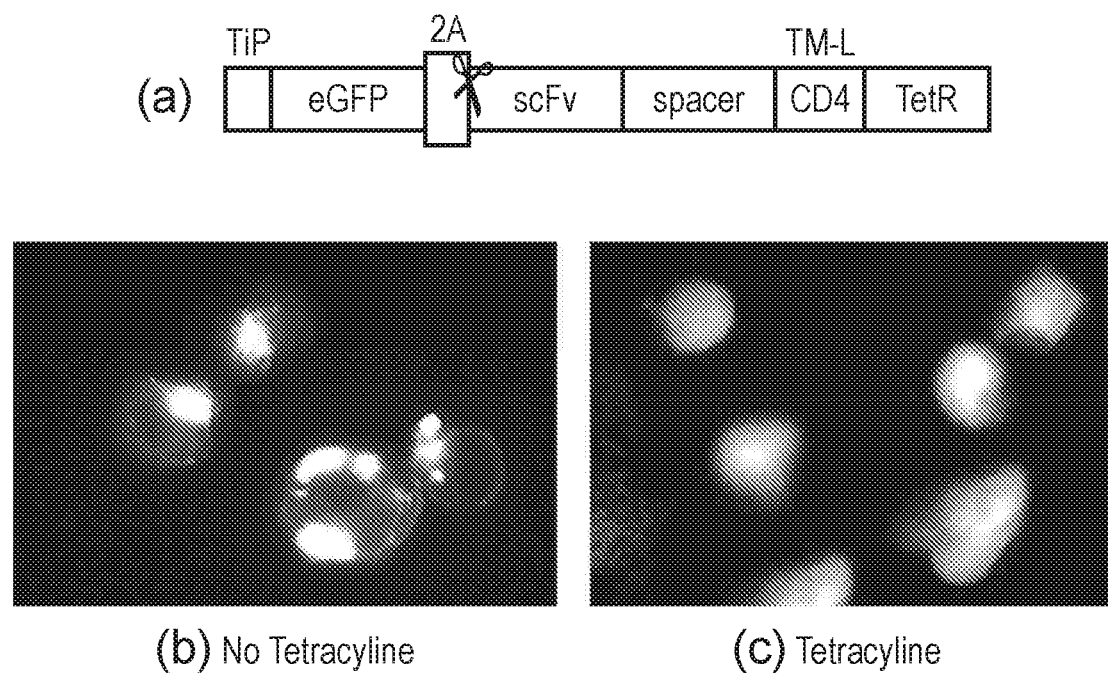
FIG. 5—Test construct with eGFP to demonstrate function of the system. (a) a bicistronic construct expressed as a single transcript which self-cleaves at the 2A site to yield: TiP fused to eGFP; and a CAR with TetR as its endodomain. (b) Fluorescent micrograph of SupT1 cells expressing this construct in the absence of tetracycline. The eGFP fluorescence can clearly be seen at the cell membrane; (c) Fluorescent micrograph of the same cells but now in the presence of tetracycline. Here, the eGFP is cytoplasmic showing that tetracycline has displaced TiP.

A bicistronic construct was expressed as a single transcript which self-cleaves at the 2A site to yield TiP fused to eGFP and a CAR with TetR as its endodomain (FIG. 5a).

Fluorescent microscopy of SupT1 cells expressing this construct in the absence of tetracycline demonstrated that eGFP fluorescence can clearly be seen at the cell membrane (FIG. 5b); whilst in the presence of tetracycline the eGFP was cytoplasmic (FIG. 5c). These data demonstrate that tetracycline has displaced TiP from the TetR CAR.

Example 2—Signalling Through the Original TetCAR System

Figure 6:
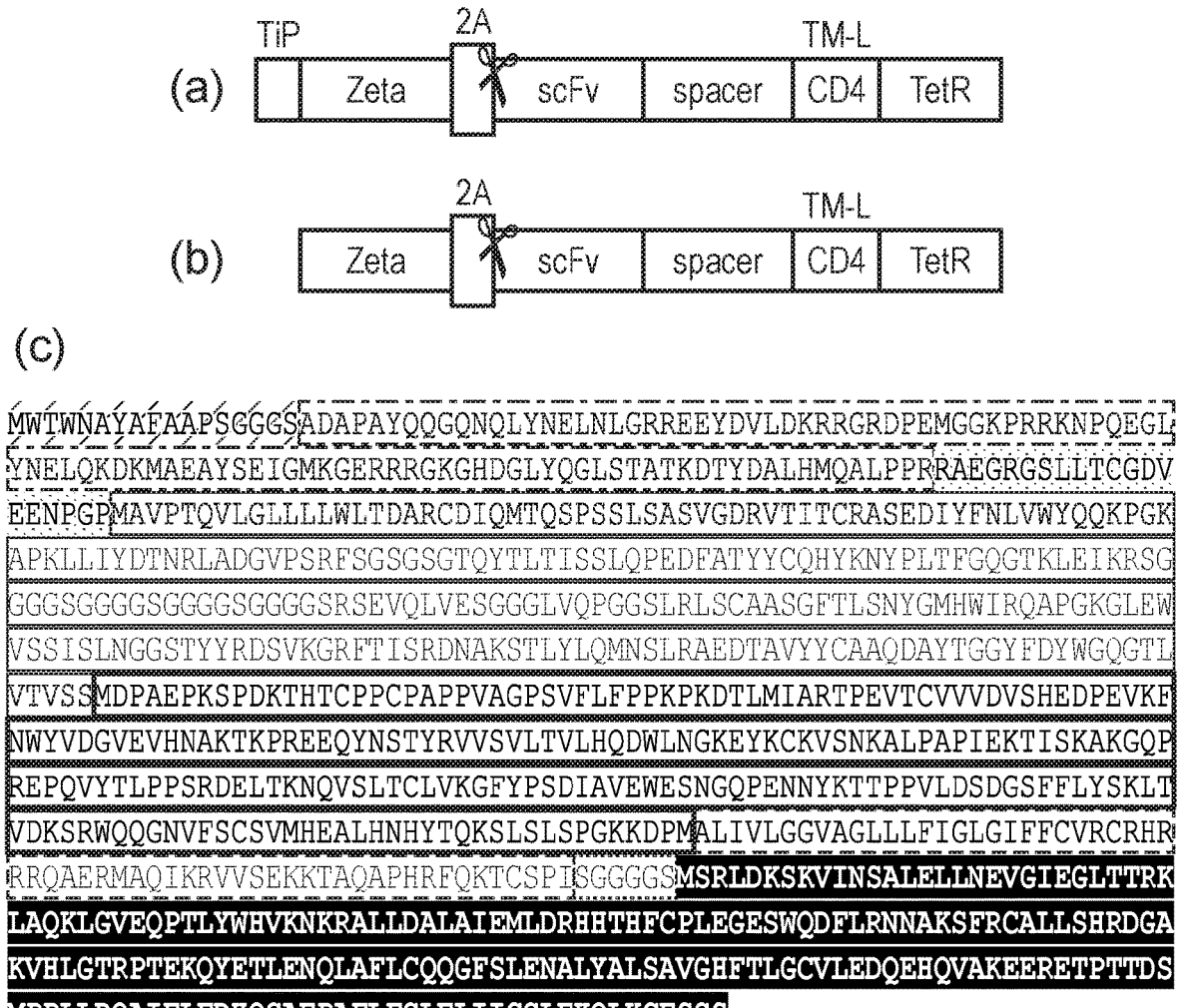
FIG. 6—Initial TetCAR construct and control (a) a bicistronic construct expressed as a single transcript which self-cleaves at the 2A site to yield: a signalling component which comprises TiP fused via a flexible linker to the endodomain of CD3-Zeta; and a receptor component which comprises a CD33 recognizing scFv, a spacer derived from the Fc domain of IgG1, a CD4 derived transmembrane and intracellular domain; and TetR. (b) a control was also constructed which was identical except TiP was absent from the signalling component. (c) annotated amino-acid sequence of the basic TetCAR is shown.

A bicistronic construct was expressed in BW5 T cells as a single transcript which self-cleaves at the 2A site to yield a signalling component which comprises TiP fused via a flexible linker to the endodomain of CD3-Zeta; and a receptor component which comprises a CD33 recognizing scFv, a spacer derived from the Fc domain of IgG1, a CD4 derived transmembrane and intracellular domain; and TetR (FIG. 6a). A control was also expressed which was identical except that TiP was absent from the signalling component (FIG. 6b).

Figure 7:
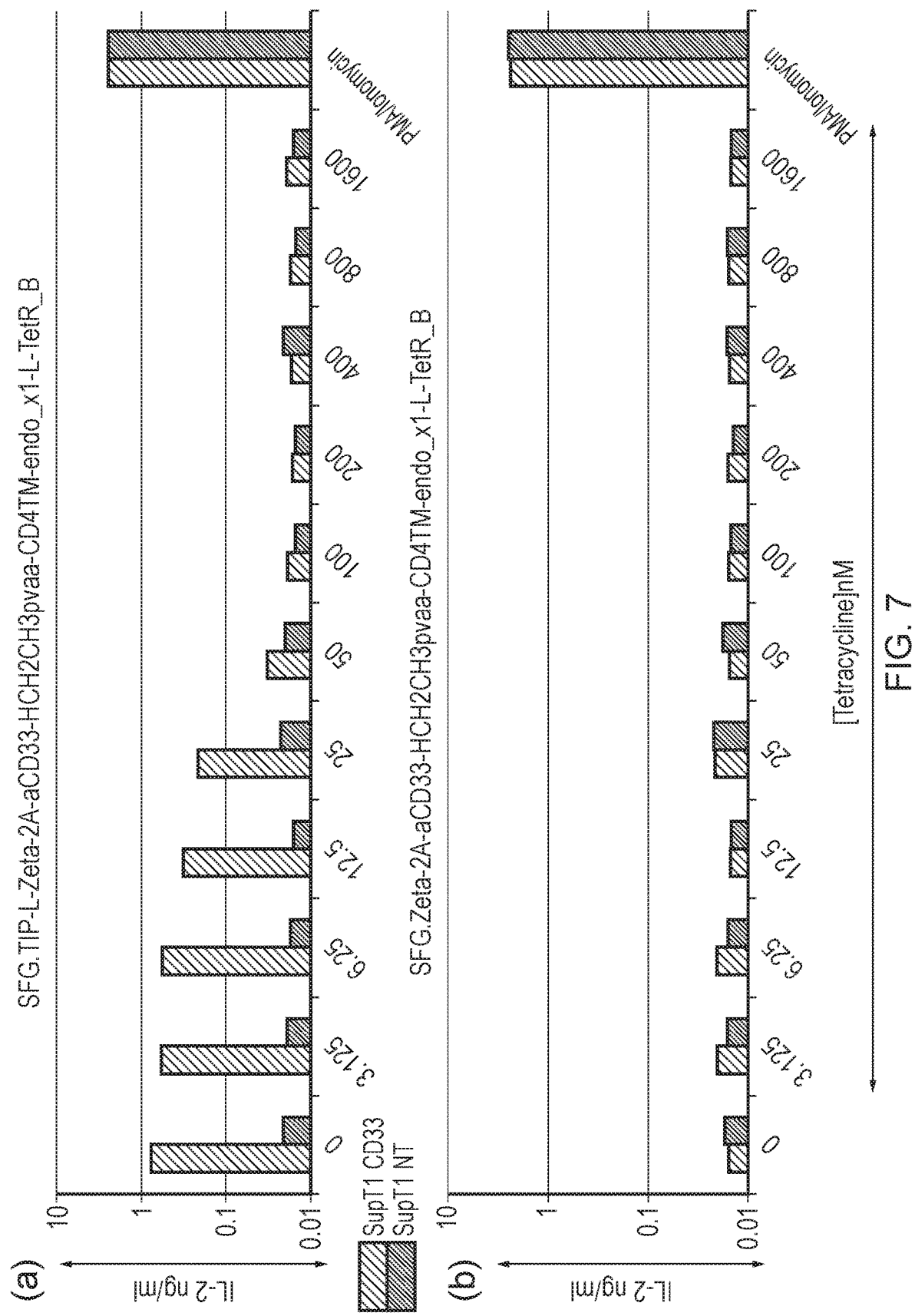
FIG. 7—Function of the initial TetR construct in comparison with control. (a) TetCAR was expressed in BW5 T-cells. These T-cells were challenged with wild-type SupT1 cells or SupT1 cells engineered to express CD33 in the absence of tetracycline or in the presence of increasing concentrations of tetracycline. T-cells challenged with wild-type SupT1 cells do not activate in either the presence or absence of Tetracyline; T-cells challenged with SupT1 cells expressing CD33 activate in the absence of Tetracycline, but activation is rapidly inhibited in the presence of tetracycline with activation fully inhibited in the presence of 100 nM of Tetracycline. (b) Control TetCAR which lacks the TiP domain was transduced into BW5. Once again, these T-cells were challenged with wild-type SupT1 cells or SupT1 cells engineered to express CD33 in the absence or in the presence of increasing concentration of Tetracycline. A lack of TiP element in the signalling component resulted in no signalling in any conditions.
Figure 8:
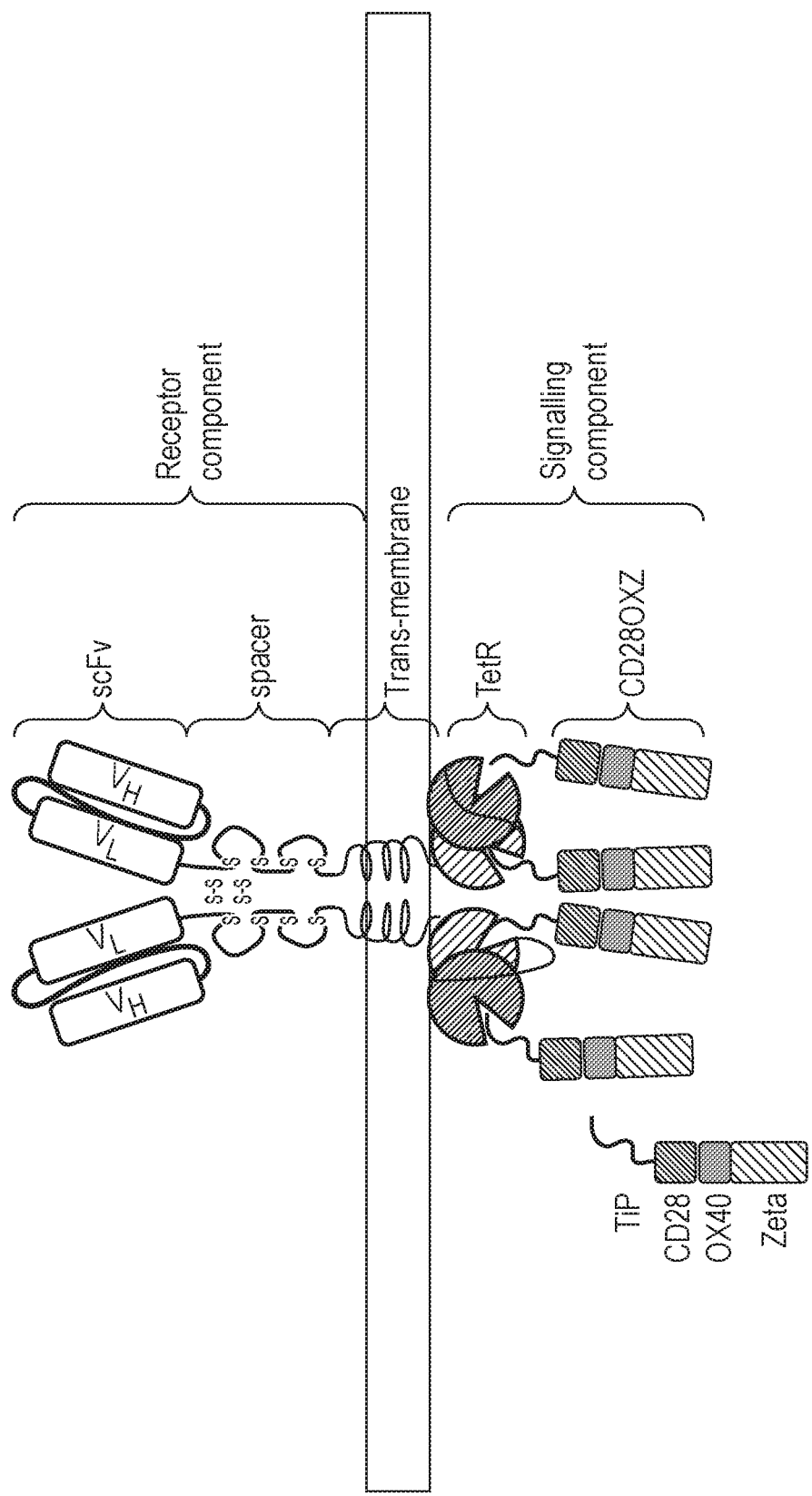
FIG. 8—Dual tetR domain tetCARs. tetR is expressed as a single-chain with two TetRs attached together. If tetR domains with differing affinity for tetracycline (and hence TiP) are used, the kinetics of Tetracycline mediated displacement of TiP can modulate the levels of signalling.

The BW5 T-cells were challenged with wild-type SupT1 cells or SupT1 cells engineered to express CD33 in the absence of tetracycline or in the presence of increasing concentrations of tetracycline. T-cells challenged with wild-type SupT1 cells did not activate in either the presence or absence of Tetracyline; T-cells challenged with SupT1 cells expressing CD33 were activated in the absence of Tetracycline, but activation is rapidly inhibited in the presence of tetracycline with activation fully inhibited in the presence of 100 nM of tetracycline (FIG. 7a).

Control TetCAR which lacks the TiP domain was also transduced into BW5. Once again, these T-cells were challenged with wild-type SupT1 cells or SupT1 cells engineered to express CD33 in the absence or in the presence of increasing concentration of Tetracycline. A lack of TiP element in signalling component resulted in no signalling in any conditions (FIG. 7b).

Example 3—Signalling of the Original TetCAR System in Primary T Cells

Figure 13:
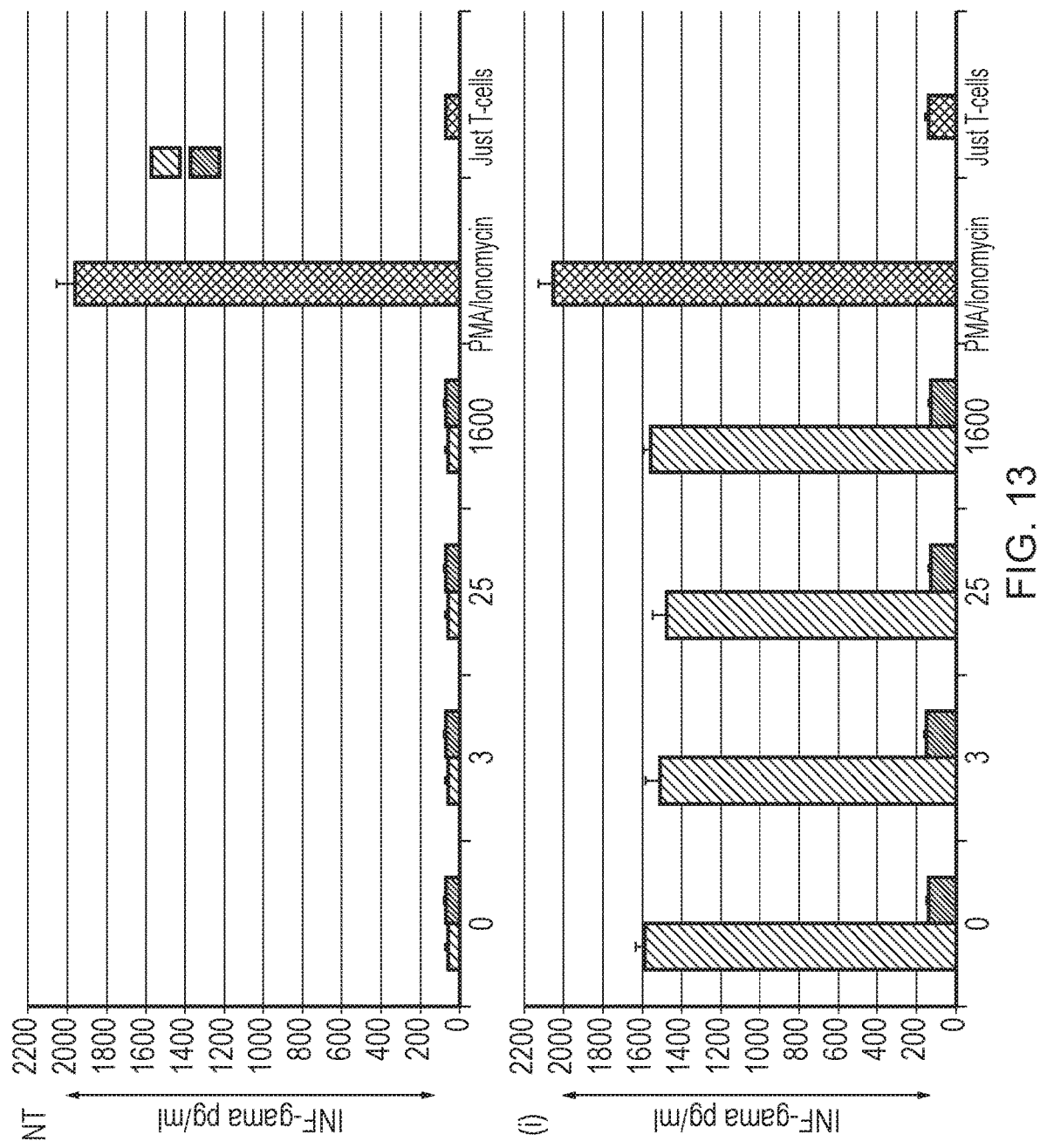
FIG. 13—Interferon-Gamma release from non-transduced T-cells, and T-cells transduced with the different CAR construct challenged ((i) Classical first generation CAR, (ii) tetCAR and (iii) control tetCAR), with SupT1 cells (red), SupT1.CD19 cells (blue) in different concentrations of Tetracyline.
Figure 13:
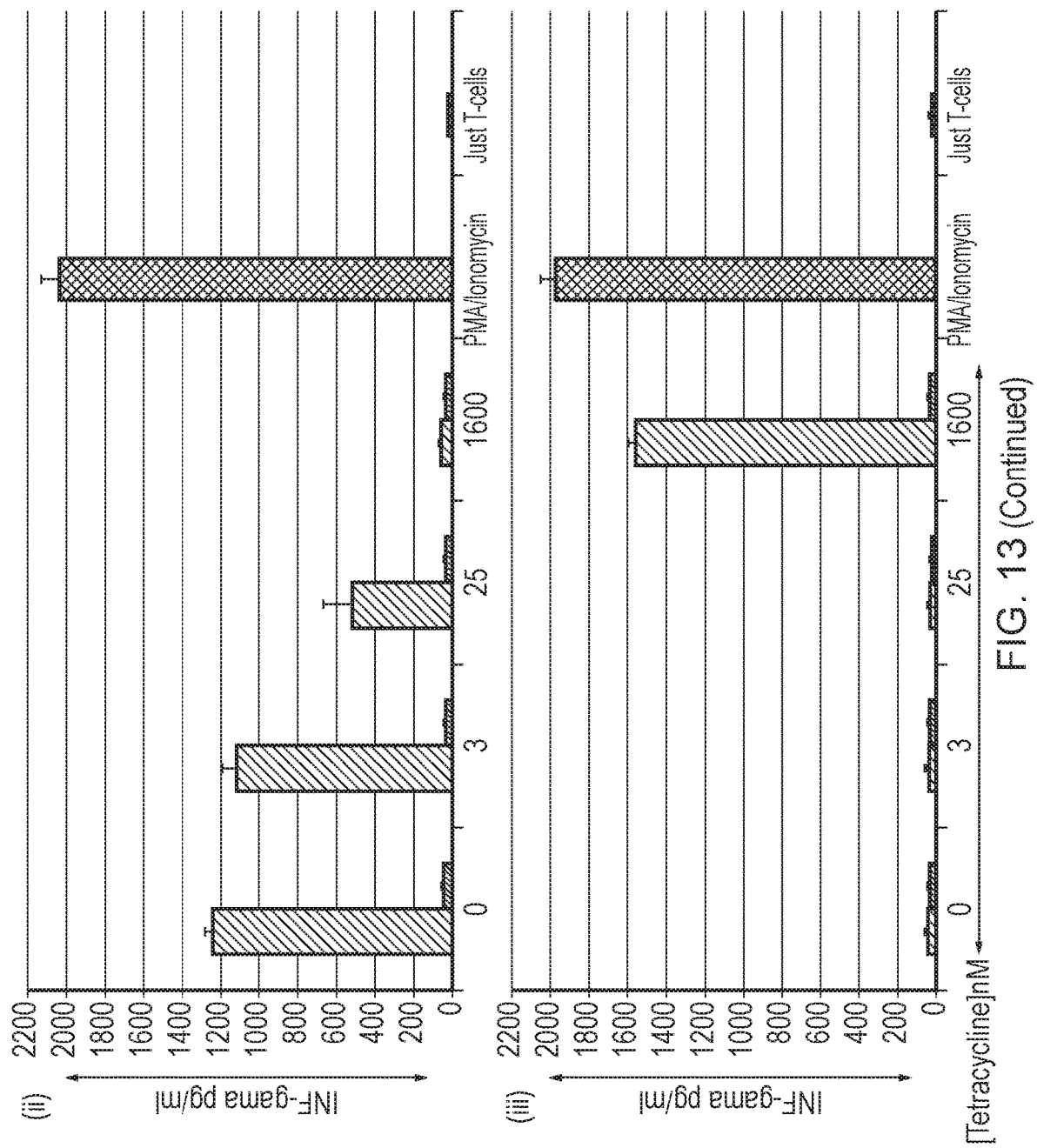

SupT1 cells (which are CD19 negative), were engineered to be CD19 positive giving target negative and positive cell lines which were as similar as possible. Primary human T-cells from 3 donors were transduced with three CAR constructs: (i) "Classical" 1st generation anti-CD19 CAR; (ii) 1st generation anti-CD19 tetCAR; (iii) Control anti-CD19 tetCAR where TiP is missing from endodomain. Non-transduced T-cells and T-cells transduced with the different CAR constructs were challenged 1:1 with either SupT1 cells or SupT1.CD19 cells in the presence of different concentrations of Tetracycline. Supernatant was sampled 48 hours after challenge. Supernatant from background (T-cells alone), and maximum (T-cells stimulated with PMA/lonomycin) was also samples. Interferon-gamma was measured in supernatants by ELISA (FIG. 13). "Classical" CAR T-cells were activated by SupT1.CD19 irrespective of tetracycline. TetCAR T-cell were activated by SupT1.CD19 cells but activation was inhibited by Tetracycline. The control TetCAR and NT T-cells did not respond to SupT1.CD19 cells.

Example 4—Killing of Target Cells

Figure 14:
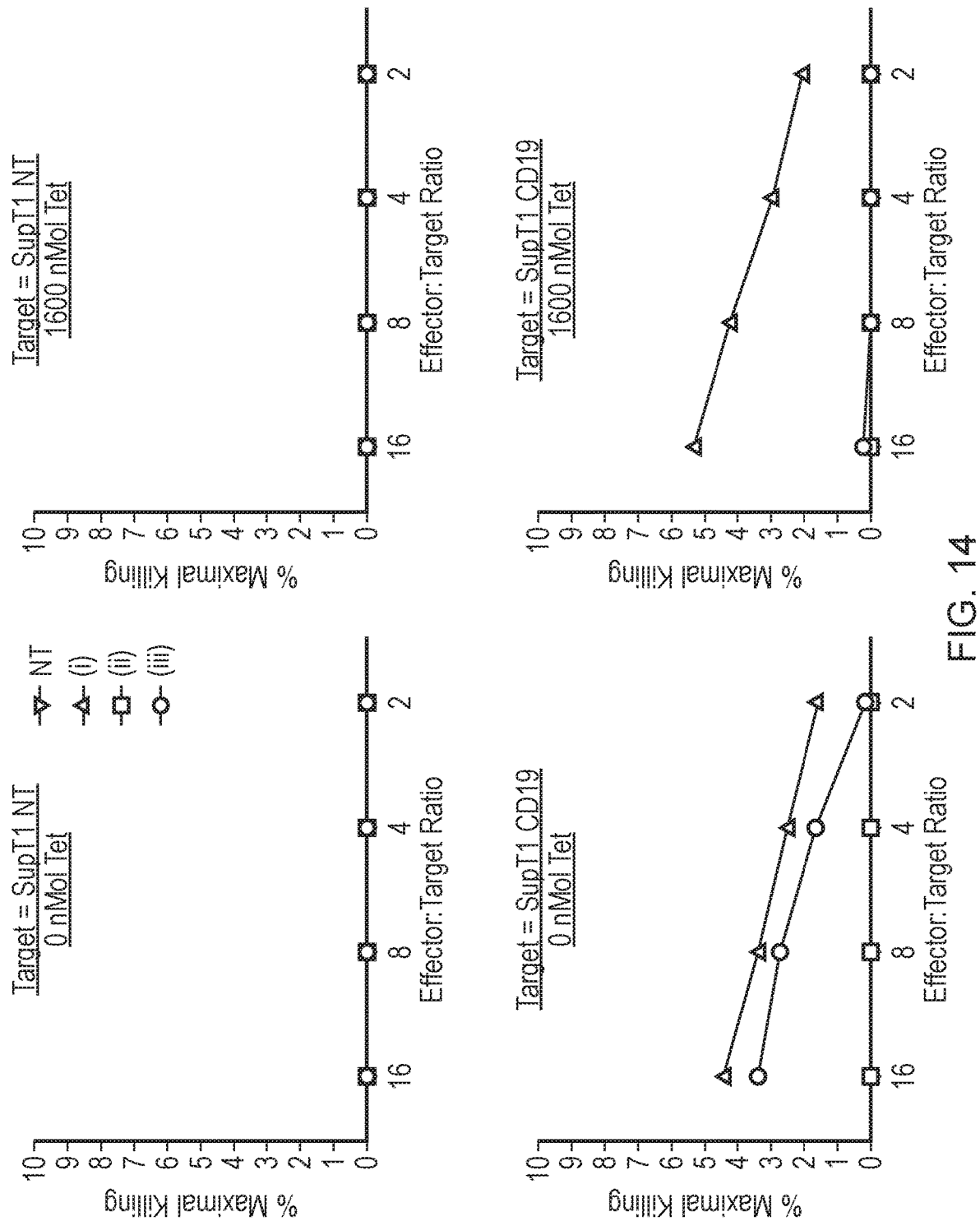
FIG. 14—Killing of target cells. A chromium release assay was used to demonstrate killing of target cells (SupT1.CD19) in the absence of tetracycline. Key: (i)—regular CAR; (ii)—control tetCAR (no TiP on endodomain); (iii)—tetCAR.
Figure 15:
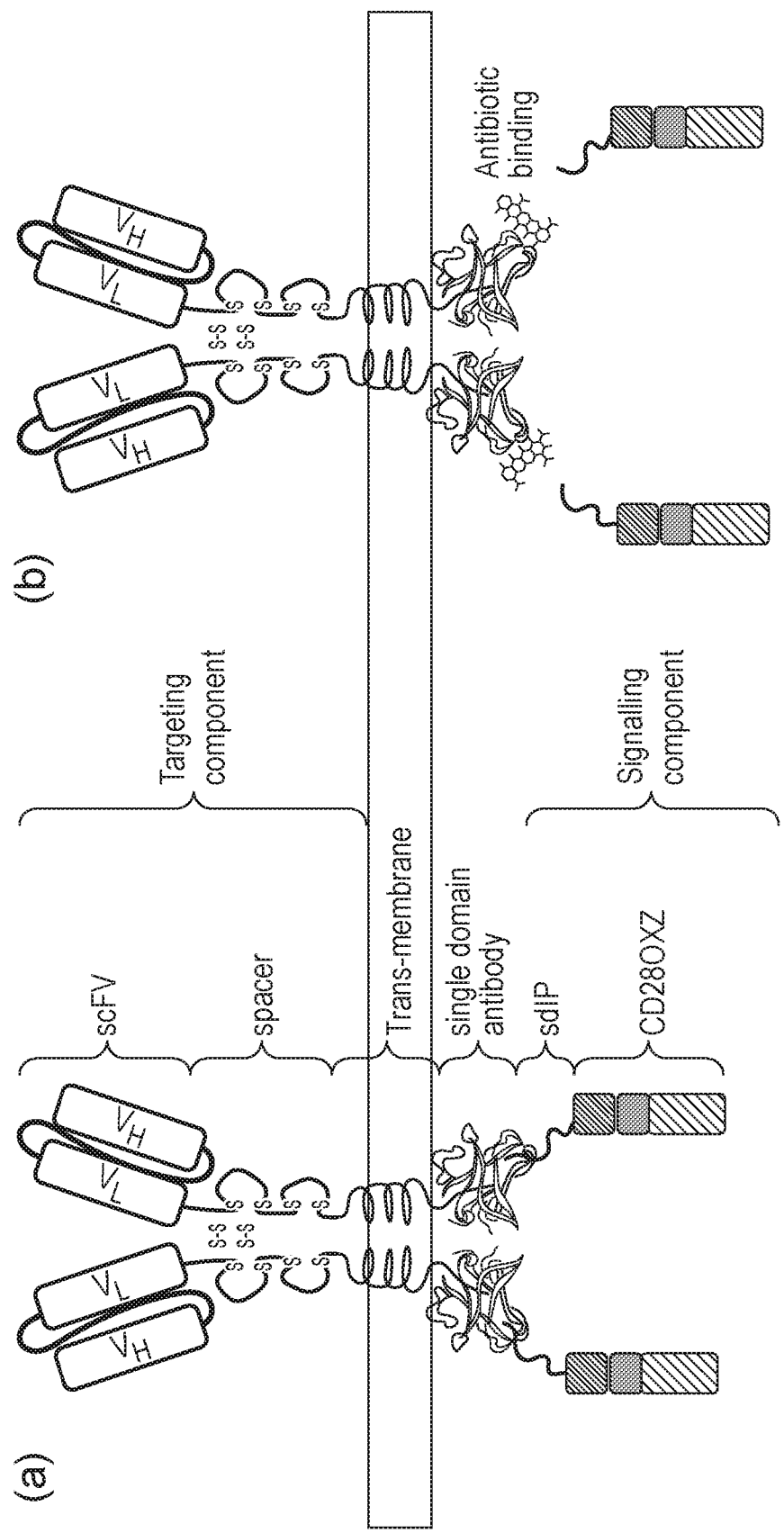
FIG. 15—A single domain binder-based CAR signalling system. (a) A membrane spanning receptor component comprises an extracellular antigen-binding domain, a transmembrane domain and an intracellular linker to a single domain antibody which binds to an antibiotic. A separate molecule, the signalling component, comprises an intracellular protein which is generated by fusion of a single domain antibody interacting peptide (sdIP) to one or several T-cell signalling domains. In the absence of the antibiotic, the receptor and the signalling components interact and in the presence of cognate antigen the system signals. (b) In the presence of the antibiotic, the single domain antibody is displaced from the sdIP and the receptor can not transmit signals even in the presence of cognate antigen.

Following on from the interferon-gamma release study described in Example 3, killing of target cells was demonstrated using a chromium release assay. SupT1 and SupT1.CD19 cells were loaded with $^{51}$Cr and incubated with control and Tet-CAR T-cells for 4 hours in the presence or absence of tetracycline. Lysis of target cells was determined by counting $^{51}$Cr in the supernatant. The results are shown in FIG. 14. It was shown that Tet-CAR T-cells lysed SupT1.CD19 target cells only in the absence of Tetracycline.

Example 5—Production of a Single Domain Antibody which Binds Minocycline

Minocycline was functionalised by the addition of a SH group linked to hexyl spacer. Functionalization occurred at the acid group located at position 10 of the minocycline molecule. 10-(6-mercaptohexyl)-minocycline was conjugated to KLH and BSA using standard maleimide coupling chemistry. Llamas were immunized at days 0, 7, 14 and 21, with 25 mg KLH—minocycline conjugate. Serum was collected prior to each injection to follow the immune response against the immunogen. At day 31 anticoagulated blood was collected for lymphocyte isolation.

IgG3 isolation from the serum of day 31 was dialysed against 0.1 M NH4HCO3, pH 8.0, before *Staphylococcus aureus* is added at a 1/50 (w/w) ratio. After incubation for 2 h and dialysis against PBS, monomeric polyclonal VHH was recovered in the flow-through of a HiTrap Protein A column. The single domain antibody (sdAb) concentration was determined spectrophotometrically.

A concentration of 3 µg/ml BSA-Minocycline in PBS and 3 ug/ml BSA alone in PBS were coated overnight at 4° C. on Maxisorb 96-well plates (Nunc). Plates were blocked with 1% (w/v) casein in PBS for 2 h at room temperature. After incubation with either the diluted total serum or purified IgG subclasses, bound sdAB was detected with rabbit camelid IgG-HRP polyclonal antibody.

A blood sample of about 200 ml was taken from a KLH-(10-6 Mercaptohexyl) minocycline immunised llama. An enriched lymphocyte population was obtained via Ficoll discontinuous gradient centrifugation. From these cells, total RNA was isolated by acid guanidium thiocyanate extraction. After first strand cDNA synthesis DNA fragments encoding HC-V fragments and part of the long or short hinge region where amplified by PCR. The amplified pool of dAb antibody sequences were digested using the restriction enzymes PstI and NotI, and ligated into the phagemid vector pSOS11.

Following construction the dAb phagemid library was determined to have an estimated size of 5×108 unique clones.

Single domain antibodies were expressed on phage after infection with M13K07. The phage library was panned for the presence of binders respectively on solid-phase BSA-(10-6 Mercaptohexyl)minocycline (10 µg/well) in wells of a microtitre plates or in solution with 100 nM biotinylated BSA-(10-6-Mercaptohexyl) minocycline in combination with streptavidin-coated magnetic beads.

Following two rounds of panning the whole phage library was assessed for enrichment against the BSA-minocycline and BSA only by phage ELISA. Positive enrichment was observed after pan 1 which was maintained after a second pan. 40 individual phage clones isolated from selections were sequenced to determine specific sdAB sequences.

The CDR sequences of 14 minocycline-specific dAbs are shown in Table 2.

TABLE 2

| CDR 1 | CDR 2 | CDR 3 |
|---|---|---|
| GRTFSSYN (SEQ ID No. 17) | ISWSGART (SEQ ID No. 18) | AAGRGWGTEAILDY (SEQ ID No. 19) |
| GRSLSSYV (SEQ ID No. 20) | ISWSGART (SEQ ID No. 18) | AAGRGWGTEAILDY (SEQ ID No. 19) |
| GRTFSSYN (SEQ ID No. 17) | ISWSGART (SEQ ID No. 18) | VAGRGWGTEAILDY (SEQ ID No. 21) |
| GRTFSNYN (SEQ ID No. 22) | INWSGGRT (SEQ ID No. 23) | AAGRGWGTEAILDY (SEQ ID No. 19) |
| GRTFSRYN (SEQ ID No. 24) | ISWSGART (SEQ ID No. 18) | AAGRGWGTEAILDY (SEQ ID No. 19) |
| GRTFSSYN (SEQ ID No. 17) | ISRSGGIT (SEQ ID No. 25) | AAGRGWGVEAILDY (SEQ ID No. 26) |
| GNIGLVSV (SEQ ID No. 27) | ITGGGST (SEQ ID No. 28) | RLVNNGRPF (SEQ ID No. 29) |
| GRLSLSSYV (SEQ ID No. 30) | ISWSGART (SEQ ID No. 18) | AAGRGWGTEAILDY (SEQ ID No. 19) |

The sequenced sdAB genes were subcloned into a vector encoding a dual H6 tag followed by a termination codon. An overnight culture of BL21 cells freshly transformed with the appropriate plasmid was used to inoculate 1 l of Terrific Broth medium containing 100 µg/ml ampicillin and 0.1% glucose. After growth at 37° C., until the optical density reached 0.75-1.0, expression was induced by the addition of 1 mM IPTG. Growth continued for an additional 16 h at 28° C. After harvesting the cells by centrifugation, the periplasmic fraction containing the sdAb was prepared. The His tag-containing fusion proteins were purified by chromatography on Ni-NTA and Superdex-75. The protein concentration of the sdAb was determined spectrophotometrically using their calculated extinction coefficients.

Kinetic analysis of the interactions between minocycline and sdAbs were measured by BIAcore. The individual VHH fragments were immobilized on a carboxymethylated dextran layer using ECD/NHS chemistry. For the determination of the kinetic constants, diluted solutions of BSA-minocyline (10-150 nM in PBS) were applied over the sensor surface. Binding traces were recorded for at least five different concentrations in duplicate. Association and dissociation rate constants were calculated using a Langmuir binding model or steady state kinetics.

Example 6—Selection of a Peptide for Use in the Intracellular Signalling Component In order to identify a peptide which binds the minocycline specific sdAb, and is competed out by minocycline, a peptide phage library (Ph.D 12 New England biolabs) is panned for the presence of peptide binders on biotinylated minocycline specific sdAb on streptavidin-coated magnetic beads. BSA conjugated minocycline in increasing concentrations is used to elute the peptide containing phage and thus enrich for populations that compete with minocycline.

Example 7—Generation of a CAR Signalling System Disruptable by Methotrexate

A single domain antibody against methotrexate has previously been described (Fanning and Horn (2011) Protein Science 20:1196-1207). The binder sequences are used for peptide phage display to generate interacting peptide as described in Example 6.

A CAR signalling system was developed using the anti-methotrexate sdAb binder in the receptor component and an interacting peptide in the intracellular signalling component and expressed in a cell.

A population of peptides specific to the anti-methotrexate sdAb binder was generated using peptide phage display. In brief, purified anti-methotrexate dAb with a His6 tag was captured on Dynabeads for His-Tag isolation and pulldown. Beads with dAb were captured and transferred to blocking buffer (2% BSA). Unconjugated beads were also blocked. A 100 fold representation of the phage display library was added to blocked beads in blocking buffer to remove non-specific phage. The blocked beads were capture via magnet and the supernatant transferred to dAb conjugated beads for selection.

CDR specific phage were eluted by addition of methotrexate at a concentration of 10-fold the estimated affinity of the respective dAb for its target. Specific phage were amplified by infection of ER2738 E. coli before precipitation. Numbers of eluted and amplified phage were titrated using serial dilution plating of infected E. coli and subsequent counting.

The protocol was repeated 3-4 times to enrich the population for peptides specific to dAb-CDRs.

The amino acid sequences of five methotrexate competing peptides are shown as SEQ ID No. 6 to 10 in Table 3.

TABLE 3

| MTX competing peptide | SEQ ID No |
|---|---|
| ACNAGHLSQC | SEQ ID No. 6 |
| ASLAITH | SEQ ID No. 7 |
| ACISLTLNRC | SEQ ID No. 8 |
| QTEKNPL | SEQ ID No. 9 |
| ACNAGHLSQC | SEQ ID No. 10 |

A construct was then generated for co-expression of a suicide gene (RQR8); a signalling component with a CD19-specific antigen binding domain and an anti-methotrexate dAb; and an intracellular signalling component comprising a dAb interacting peptide and CD3 zeta (FIG. 16A).

The CAR system expressed by the construct is shown in FIG. 16B Signal abrogation and tenability with methotrexate was then investigated.

BW5 cells were transduced with methotrexate dAb based constructs or controls. Cells were stained with 7-AAD and anti-h-Fc to assess the efficiency of the transduction.

The cells were gated on single cell population and then the 7-AAD negative population (live cells). Cells stained positively for human-Fc, within the live cells corresponds to the transduced cells expressing the methotrexate constructs.

BW5 cells transduced with split CAR constructs were co-cultured with SupT1 cells expressing CD19 or untransduced SupT1 cells at a 1:1 ratio. The secretion of the cytokine IL-2 was measured after 48 hours in the presence or absence of methotrexate.

Example 8—Generation of a CAR Signalling System Disruptable by Caffeine

A single domain antibody which binds specifically to caffeine was generated by immunisation of llamas, using methodology similar to that described in Example 5.

The caffeine dAb amino acid sequence is shown below as SEQ ID No. 11. The three CDRs are underlined and in bold.

Sequence ID No. 11
EVQLQASGGGLVQAGGSLRLSCTASGRTGTIYSMAWFRQAPGKEREFLAT
VGWSSGITYYMDSVKGRFTISRDNAKNSAYLQMNSLKPEDTAVYYCTATR
AYSVGYDYWGQGTQVTVSS A population of peptides specific to the anti-caffeine sdAb binder was generated using peptide phage display, using the method described in Example 6.

The amino acid sequences of five caffeine competing peptides are shown as SEQ ID No. 12 to 16 in Table 4.

TABLE 4

| Caffeine competing peptide | SEQ ID No |
|---|---|
| HTLNKPP | SEQ ID No. 12 |
| DLSIGNH | SEQ ID No. 13 |
| HDSPTAA | SEQ ID No. 14 |
| YPDVPLA | SEQ ID No. 15 |
| ACTYLNSAKC | SEQ ID No. 16 |

Signal abrogation and tenability with caffeine was then investigated.

BW5 cells were transduced with caffeine dAb based constructs or controls. Cells were stained with 7-AAD and anti-h-Fc to assess the efficiency of the transduction.

The cells were gated on single cell population and then the 7-AAD negative population (live cells). Cells stained positively for human-Fc, within the live cells corresponds to the transduced cells expressing the caffeine constructs.

BW5 cells transduced with split CAR constructs were co-cultured with SupT1 cells expressing CD19 or untransduced SupT1 cells at a 1:1 ratio. The secretion of the cytokine IL-2 was measured after 48 hours in the presence or absence of caffeine.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A chimeric antigen receptor (CAR) system comprising:
   (i) a receptor component comprising an antigen binding domain, a transmembrane domain and first binding domain which comprises a single domain binder which binds an agent, and
   (ii) an intracellular signalling component comprising a signalling domain and a second binding domain which binds the single domain binder of the first binding domain of the receptor component;
   wherein binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain, and wherein the agent is:

caffeine and the single domain binder is a dAb comprising:
  (a) CDR1 having the amino acid sequence TIYSMA (SEQ ID NO: 31), CDR2 having the amino acid sequence TVGWSSGITYYMDSVKG (SEQ ID NO: 32), and CDR3 having the amino acid sequence TRAYSVGYDY (SEQ ID NO: 33); or
  (b) the amino acid sequence of SEQ ID NO: 11, and the second binding domain comprises:

```
HTLNKPP,     (SEQ ID NO. 12)

DLSIGNH,     (SEQ ID NO. 13)

HDSPTAA,     (SEQ ID NO. 14)

YPDVPLA, or  (SEQ ID NO. 15)

ACTYLNSAKC.  (SEQ ID NO. 16)
```

2. A nucleic acid sequence encoding a CAR signalling system according to claim 1, wherein the receptor component and signalling component are co-expressed with a self-cleaving peptide which is cleaved between the receptor component and the signalling component after translation of the components.

3. A vector comprising a nucleic acid sequence according to claim 2.

4. A chimeric antigen receptor (CAR) system comprising;
  (i) an intracellular signalling component comprising a signalling domain and a first binding domain comprises a single domain binder, and
  (ii) a receptor component comprising an antigen binding domain, a transmembrane domain and second binding domain which binds the single domain binder of the intracellular signalling component;

wherein binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain and wherein the agent is:

caffeine and the single domain binder is a dAb comprising:
  (a) CDR1 having the amino acid sequence TIYSMA (SEQ ID NO: 31), CDR2 having the amino acid sequence TVGWSSGITYYMDSVKG (SEQ ID NO: 32), and CDR3 having the amino acid sequence TRAYSVGYDY (SEQ ID NO: 33); or
  (b) the amino acid sequence of SEQ ID NO: 11, and the second binding domain comprises:

```
HTLNKPP,     (SEQ ID NO. 12)

DLSIGNH,     (SEQ ID NO. 13)

HDSPTAA,     (SEQ ID NO. 14)

YPDVPLA, or  (SEQ ID NO. 15)

ACTYLNSAKC.  (SEQ ID NO. 16)
```

5. A nucleic acid sequence encoding a CAR signalling system according to claim 4, wherein the receptor component and signalling component are co-expressed with a self-cleaving peptide which is cleaved between the receptor component and the signalling component after translation of the components.

6. A vector comprising a nucleic acid sequence according to claim 5.

7. A cell which expresses
  (i) a receptor component comprising an antigen binding domain, a transmembrane domain and first binding domain which comprises a single domain binder which binds an agent, and
  (ii) an intracellular signalling component comprising a signalling domain and a second binding domain which binds the single domain binder of the first binding domain of the receptor component;

wherein binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain and wherein the agent is:

caffeine and the single domain binder is a dAb comprising:
  (a) CDR1 having the amino acid sequence TIYSMA (SEQ ID NO: 31), CDR2 having the amino acid sequence TVGWSSGITYYMDSVKG (SEQ ID NO: 32), and CDR3 having the amino acid sequence TRAYSVGYDY (SEQ ID NO: 33); or
  (b) the amino acid sequence of SEQ ID NO: 11, and the second binding domain comprises:

```
HTLNKPP,     (SEQ ID NO. 12)

DLSIGNH,     (SEQ ID NO. 13)

HDSPTAA,     (SEQ ID NO. 14)

YPDVPLA, or  (SEQ ID NO. 15)

ACTYLNSAKC.  (SEQ ID NO. 16)
```

8. A pharmaceutical composition comprising a plurality of cells according to claim 7.

9. A method for making a cell according to claim 7, which comprises the step of introducing into the cell a nucleic acid sequence encoding or a vector encoding a CAR signalling system comprising:

(i) a receptor component comprising an antigen binding domain, a transmembrane domain and first binding domain which comprises a single domain binder which binds an agent, and (ii) an intracellular signalling component comprising a signalling domain and a second binding domain which binds the single domain binder of the first binding domain of the receptor component;

wherein binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain, and wherein the receptor component and signalling component are co-expressed with a self-cleaving peptide which is cleaved between the receptor component and the signalling component after translation of the components.

10. A cell which expresses (i) an intracellular signalling component comprising a signalling domain and a first binding domain comprises a single domain binder, and (ii) a receptor component comprising an antigen binding domain, a transmembrane domain and second binding domain which binds the single domain binder of the intracellular signalling component;

wherein binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain and wherein the agent is:
caffeine and
the single domain binder is a dAb comprising:
(a) CDR1 having the amino acid sequence TIYSMA (SEQ ID NO: 31), CDR2 having the amino acid sequence TVGWSSGITYYMDSVKG (SEQ ID NO: 32), and CDR3 having the amino acid sequence TRAYSVGYDY (SEQ ID NO: 33); or
(b) the amino acid sequence of SEQ ID NO: 11,
and the second binding domain comprises:

```
                                      (SEQ ID NO. 12)
    HTLNKPP, (SEQ ID NO. 13)
    DLSIGNH, (SEQ ID NO. 14)
    HDSPTAA, (SEQ ID NO. 15)
    YPDVPLA, or (SEQ ID NO. 16)
    ACTYLNSAKC.
```

11. A pharmaceutical composition comprising a plurality of cells according to claim 10.

12. A method for making a cell according to claim 10, which comprises the step of introducing into the cell a nucleic acid sequence encoding or a vector encoding a CAR signalling system comprising:

(i) an intracellular signalling component comprising a signalling domain and a first binding domain comprises a single domain binder, and (ii) a receptor component comprising an antigen binding domain, a transmembrane domain and second binding domain which binds the single domain binder of the intracellular signalling component;

wherein binding of the first and second binding domains is disrupted by the presence of an agent, such that in the absence of the agent, the receptor component and the signalling component heterodimerize and binding of the antigen binding domain to antigen results in signalling through the signalling domain; whereas in the presence of the agent, the receptor component and the signalling component do not heterodimerize and binding of the antigen binding domain to antigen does not result in signalling through the signalling domain, and wherein the receptor component and signalling component are co-expressed with a self-cleaving peptide which is cleaved between the receptor component and the signalling component after translation of the components.

* * * * *